United States Patent
Kwok et al.

(10) Patent No.: US 12,092,710 B2
(45) Date of Patent: Sep. 17, 2024

(54) MRI TRACKING DEVICE DESIGN, FABRICATION, AND METHODS OF USE FOR MRI-GUIDED ROBOTIC SYSTEM

(71) Applicant: THE UNIVERSITY OF HONG KONG, Hong Kong (CN)

(72) Inventors: Ka Wai Kwok, Hong Kong (CN); Chim Lee Cheung, Hong Kong (CN); Di-Lang Justin Ho, Hong Kong (CN); Ziyan Guo, Guangxi (CN); Hing Chiu Chang, Macau (CN); Varut Vardhanabhuti, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 919 days.

(21) Appl. No.: 16/965,888

(22) PCT Filed: Mar. 11, 2019

(86) PCT No.: PCT/IB2019/051945
§ 371 (c)(1),
(2) Date: Jul. 29, 2020

(87) PCT Pub. No.: WO2019/171357
PCT Pub. Date: Sep. 12, 2019

(65) Prior Publication Data
US 2021/0003644 A1    Jan. 7, 2021

Related U.S. Application Data

(60) Provisional application No. 62/640,798, filed on Mar. 9, 2018.

(51) Int. Cl.
*G01R 33/28* (2006.01)
*A61B 5/055* (2006.01)
(Continued)

(52) U.S. Cl.
CPC ............ *G01R 33/286* (2013.01); *A61B 5/055* (2013.01); *A61B 90/39* (2016.02); *G01B 7/28* (2013.01);
(Continued)

(58) Field of Classification Search
CPC ............ G01R 33/287; G01R 33/34084; G01R 33/3642; G01R 33/4007; A61B 5/055;
(Continued)

(56) References Cited

U.S. PATENT DOCUMENTS

| 6,847,837 B1 * | 1/2005 | Melzer | A61B 5/06 |
| | | | 324/309 |
| 9,638,769 B2 * | 5/2017 | Wirtz | G01R 33/287 |

(Continued)

FOREIGN PATENT DOCUMENTS

| CN | 1726401 A | 1/2006 |
| CN | 102892347 A | 1/2013 |

(Continued)

OTHER PUBLICATIONS

Alipour, Akbar, et al. "An inductively coupled ultra-thin, flexible, and passive RF resonator for MRI marking and guiding purposes: Clinical feasibility." Magnetic Resonance in Medicine 80.1 (2018): 361-370. (Year: 2018).*

(Continued)

*Primary Examiner* — Sean D Mattson
(74) *Attorney, Agent, or Firm* — Saliwanchik, Lloyd & Eisenschenk

(57) ABSTRACT

An MR marker (501, 601, 803, 902) for magnetic resonance imaging (MRI) guided intervention and method of fabricating same. The tracking device can be integrated with an MRI-guided robotic system to provide precise positional tracking of the interventional tools and robotic components, allowing safe operation inside the human body. The MR (Continued)

tracking device includes a plurality of stacked flexible printed circuit boards; a plurality of flat planar spirals comprised of a non-ferromagnetic material and directly disposed on a top surface and a bottom surface side of each flexible printed circuit board, a biocompatible, non-ferromagnetic material encapsulating the flexible printed circuit boards; and an adhesive bonding the flexible printed circuit boards. In another aspect, an orientation-independent device is provided including three or more markers (501, 601, 803, 902) in an array around a cylindrical substrate.

18 Claims, 19 Drawing Sheets

(51) Int. Cl.
| | | |
|---|---|---|
| A61B 90/00 | (2016.01) | |
| G01B 7/28 | (2006.01) | |
| G01B 11/24 | (2006.01) | |
| A61B 34/20 | (2016.01) | |
| G01R 33/34 | (2006.01) | |
| G01R 33/36 | (2006.01) | |

(52) U.S. Cl.
CPC ...... *G01B 11/24* (2013.01); *A61B 2034/2061* (2016.02); *A61B 2090/3958* (2016.02); *G01R 33/287* (2013.01); *G01R 33/34084* (2013.01); *G01R 33/3642* (2013.01)

(58) Field of Classification Search
CPC . A61B 5/062; A61B 90/39; A61B 2034/2061; A61B 2090/3958; G01B 7/28; G01B 11/24
See application file for complete search history.

(56) References Cited

U.S. PATENT DOCUMENTS

| | | | | |
|---|---|---|---|---|
| 2006/0173284 | A1* | 8/2006 | Ackerman | G01R 33/34084 600/422 |
| 2007/0043288 | A1* | 2/2007 | Mueller | A61B 5/055 600/411 |
| 2014/0171784 | A1 | 6/2014 | Ooi et al. | |
| 2015/0002256 | A1* | 1/2015 | Bourns | H01F 17/0013 336/200 |
| 2019/0038365 | A1* | 2/2019 | Soper | A61B 6/547 |

FOREIGN PATENT DOCUMENTS

| | | |
|---|---|---|
| CN | 103268873 A | 8/2013 |
| CN | 105359233 A | 2/2016 |

OTHER PUBLICATIONS

Gedroyc, W.M.W., "Interventional magnetic resonance imaging", BJU International, 2000, 86(Suppl. 1): 174-180.

Bock, M. et al., "MR-Guided Intravascular Procedures: Real-Time Parameter Control and Automated Slice Positioning With Active Tracking Coils", Journal of Magnetic Resonance Imaging, 2004, 19:580-589, Wiley-Liss, Inc.

Tsekos, N.V. et al., "Magnetic Resonance-Compatible Robotic and Mechatronics Systems for Image-Guided Interventions and Rehabilitation: A Review Study", Annual Review of Biomedical Engineering, 2007, 9:351-387, Annual Reviews.

Dumoulin, C.L. et al., "Real-Time Position Monitoring of Invasive Devices Using Magnetic Resonance", MRM, 1993, 29:411-415, Williams & Wilkins.

Chen, Y. et al., "Design and Fabrication of MR-Tracked Metallic Stylet for Gynecologic Brachytherapy", IEEE/ASME Transactions On Mechatronics, Apr. 2016, 21(2):956-962, IEEE.

Quick, H.H. et al., "Interventional Magnetic Resonance Angiography with No Strings Attached: Wireless Active Catheter Visualization", Magnetic Resonance in Medicine, 2005, 53:446-455, Wiley-Liss, Inc.

Ladd, M.E. et al., "Reduction of Resonant RF Heating in Intravascular Catheters Using Coaxial Chokes", Magnetic Resonance in Medicine, 2005, 43:615-619, Wiley-Liss, Inc.

Weiss, S. et al., "Transmission Line for Improved RF Safety of Interventional Devices", Magnetic Resonance in Medicine, 2005, 54:182-189, Wiley-Liss, Inc.

Weiss, S. et al., "In Vivo Safe Catheter Visualization and Slice Tracking Using an Optically Detunable Resonant Marker", Magnetic Resonance in Medicine, 2004, 52:860-868, Wiley-Liss, Inc.

Wong, E.Y. et al., "An Optical System for Wireless Detuning of Parallel Resonant Circuits", Journal of Magnetic Resonance Imaging, 2000, 12:632-638, Wiley-Liss, Inc.

Omary, R.A. et al., "Real-Time MR Imaging-guided Passive Catheter Tracking with Use of Gadolinium-filled Catheters", JVIR, 2000, 11:1079-1085.

Unal, O. et al., "A Rapid 2D Time-Resolved Variable-Rate κ-space Sampling MR Technique for Passive Catheter Tracking During Endovascular Procedures", MRM, 1998, 40:356-362, Williams & Wilkins.

Wacker, F.K. et al., "Magnetic Resonance-Guided Vascular Catheterization: Feasibility Using a Passive Tracking Technique at 0.2 Telsa in a Pig Model", Journal of Magnetic Resonance Imaging, 1999, 10:841-844, Wiley-Liss, Inc.

Nitz, W.R. et al., "On the Heating of Linear Conductive Structures as Guide Wires and Catheters in Interventional MRI", Journal of Magnetic Resonance Imaging, 2001, 13:105-114, Wiley-Liss, Inc.

Nitz, W.R. et al., "Specific Absorption Rate as a Poor Indicator of Magnetic Resonance-Related Implant Heating", Investigative Radiology, Dec. 2005, 40(12):773-776, Lippincott Williams & Wilkins.

Buecker, A. et al., "Safety of MRI-guided vascular interventions", Minimally Invasive Therapy, 2006, 15(2):65-70, Taylor & Francis.

Ooi, M.B. et al., "Prospective Motion Correction Using Inductively Coupled Wireless RF Coils", Magnetic Resonance in Medicine, 2013, 70:639-647, Wiley Periodicals, Inc.

Hurley, W.G. et al., "Calculation of Self- and Mutual Impedances in Planar Sandwich Inductors", IEEE Transactions On Magnetics, May 1997, 33(3):2282-2290, IEEE.

Hurley, W.G. et al., "Impedance Formulas for Planar Magnetic Structures with Spiral Windings", IEEE Transactions On Industrial Electronics, Apr. 1999, 46(2):271-278, IEEE.

Babic, S. et al., "Improvement in Calculation of the Self- and Mutual Inductance of Thin-Wall Solenoids and Disk Coils", IEEE Transactions On Magnetics, Jul. 2000, 36(4):1970-1975, IEEE.

Babic, S. et al., "Mutual Inductance Calculation Between Circular Filaments Arbitrarily Positioned in Space: Alternative to Grover's Formula", IEEE Transactions On Magnetics, Sep. 2010, 46(9):3591-3600, IEEE.

Babic, S. et al., "New Analytic-Numerical Solutions for the Mutual Inductance of Two Coaxial Circular Coils With Rectangular Cross Section in Air", IEEE Transactions On Magnetics, Jun. 2006, 42(6):1661-1669, IEEE.

Hurley, W.G. et al., "A Unified Approach to the Calculation of Self- and Mutual-Inductance for Coaxial Coils in Air", IEEE Transactions On Power Electronics, Nov. 2015, 30(11):6155-6162, IEEE.

Greenhouse, H.M. et al., "Design of Planar Rectangular Microelectronic Inductors", IEEE Transactions On Parts, Hybrids, and Packaging, Jun. 1974, PHP-10(2):101-109, IEEE.

Jow, U.M. et al., "Modeling and Optimization of Printed Spiral Coils in Air, Saline, and Muscle Tissue Environments", IEEE Transactions On Biomedical Circuits and Systems, Oct. 2009, 3(5):339-347, IEEE.

Rea, M. et al., "Sub-pixel localization of passive micro-coil fiducial markers in interventional MRI", Magn Reson Mater Phy, 2009, 22:71-76, ESMRMB 2008.

International Search Report dated Jun. 27, 2019 in International Application No. PCT/IB2019/051945.

\* cited by examiner

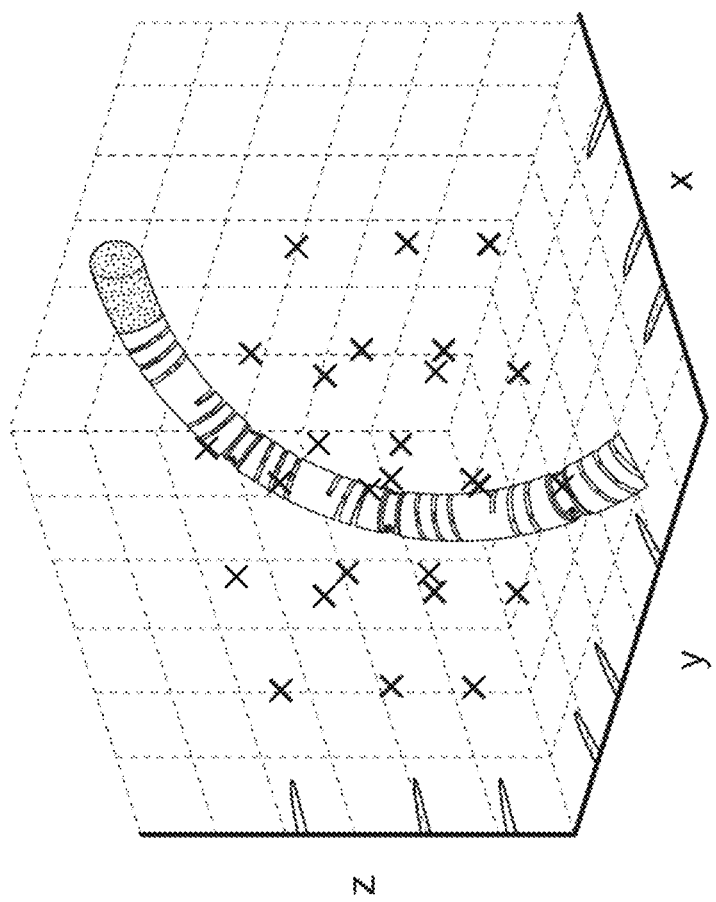
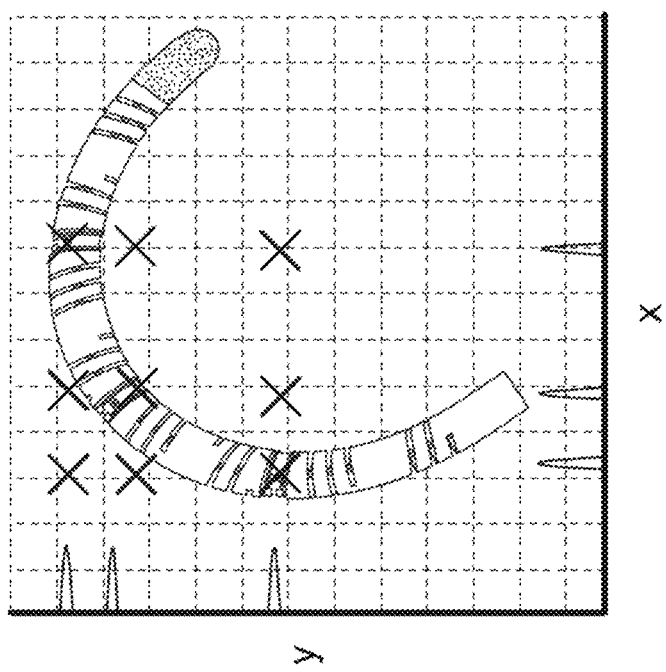
 Possible peak location
FIG. 7

DESIGN SPECIFICATIONS OF THE MULTILAYER INDUCTOR

| PARAMETERS | SYMBOL | CHARACTERISTICS |
|---|---|---|
| Maximum coil outer diameter | $d_{out}$ | 5 mm |
| Minimum coil inner diameter | $d_{in}$ | 0.53 mm |
| Minimum conductor width | $w$ | 2.4 mil |
| Minimum conductor spacing | $s$ | 2.4 mil |
| Conductor thickness | $t_{cu}$ | 12 um |
| Conductor material properties (resistivity, permeability) | $\rho, \mu$ | ~ 17 nΩm, 1 |
| Adhesive thickness | $t_{ad}$ | 25 um |
| Adhesive dielectric constant | $\varepsilon_{ad}$ | 3.5 (epoxy) |
| Coverlay thickness | $t_{cov}$ | 27.5 um |
| Substrate thickness | $t_s$ | 25 um |
| Substrate dielectric constant | $\varepsilon_s$ | 3.5 (polyimide) |

FIG. 17

MRI TRACKING DEVICE DESIGN, FABRICATION, AND METHODS OF USE FOR MRI-GUIDED ROBOTIC SYSTEM

CROSS-REFERENCE TO RELATED APPLICATIONS

This application is the U.S. national stage application of PCT/IB2019/051945, filed Mar. 11, 2019, which claims priority from U.S. Provisional Patent Application Ser. No. No. 62/640,798 filed Mar. 9, 2018, the disclosure of each of which is incorporated herein by reference in its entirety.

FIELD OF INVENTION

Embodiments of the subject invention pertain to MRI-based tracking devices. In particular, MRI-based tracking devices for use with MRI-guided robotic systems.

BACKGROUND

Magnetic resonance imaging (MRI) guided intervention is playing an increasingly important role in reshaping current interventional practices that use computed tomography (CT) or X-ray fluoroscopy. This trend can be attributed to the unique advantages of MRI, such as high intensity contrast in soft tissues and zero ionizing radiation. MRI has great potential for integration with robotic devices by using quantitative scanning data provided by the MRI. Despite the benefits of an MR-guided interventional approach, there are several difficulties that inhibit its widespread use. The first difficulty lies with the interaction with the MRI system. Specifically, device localization and pulse sequence design are challenging compared to conventional image-guided intervention. Additionally, the design and fabrication of MR-compatible devices is challenging, as the restrictive environment inside the MRI bore disallows the use of ferromagnetic metals. The use of such material during MRI causes significant artifacts, which can distort and deteriorate the overall image quality.

The combination of positional sensing and actuation can not only provide higher patient accessibility under closed-bore MRI scanners, but also enable the robotic system to perform intravascular interventional procedures such as needle, catheter, and stylet insertion in accordance of desired path or targeting locations. The methods of a MR positional tracking system can be broadly classified as wired tracking: active coil or semi-active coil; and wireless tracking: passive or tuned fiducial marker tracking.

Active coil tracking utilizes a micro coil unit connected to a receiver electronic system via coaxial cables that can actively "pick up" the MR gradient field along the three principal axes. The geometrical location of the tracking coil can be calculated from a tracking pulse sequence employing 1D projection readouts. Localization of the coils can be achieved within a few milliseconds, thus enabling a high frame rate of tracking. The optimal tracking performance can be attained in high resolution of 0.6×0.6×0.6 $mm^3$, and a high sampling rate at 40 Hz. Although this tracking approach is reliable and robust when providing position information, the conductive wires used can act as RF antennae and cause heating, which may damage the device or harm the patient. Several solutions have been proposed to solve the heating problem, such as quarter-wavelength coaxial chokes, and integration of transformers into the transmission line. On the other hand, semi-active coil tracking was proposed by replacing the conductive wires with optical fiber to control the resonant frequency of the coil. The RF behavior of the coil can be changed between two states with the photodiode connected in parallel, thus acting as an optical switch. However, such incremental electronic components would further complicate the design and fabrication, increasing the complexity of the overall system.

Passive tracking utilizes either positive or negative contrast materials. The corresponding 3D position of such markers is usually depicted in the image domain. Automatic tracking requires complicated MR sequences, as well as more computation time to process susceptibility artifacts in the high-resolution images for fast and accurate localization. Tracking based on passive markers may also encounter difficulties when multiple markers are in close proximity to each other, or when markers are out of the imaging site/slice, despite the uses of advanced image recognition techniques.

Lastly, tuned fiducial tracking markers are a specialized circuit with resonant frequency at the MRI scanner's Larmor frequency. The fiducial tracking marker can be deployed without additional hardware or electrical wired connection with the MRI scanner, and inductively couple to the MRI scanner's receiver coils. This offers simpler integration, a smoother surgical workflow, and avoids the risk of radio-frequency (RF) induced heating.

BRIEF SUMMARY

Embodiments of the subject invention relate in general to the design and fabrication of a tracking device used with magnetic resonance imaging (MRI) systems, and its methods of use for MRI-guided robotic systems. The MR tracking device can provide the geometrical location inside the magnetic resonance imaging system in real time, and the obtained geometrical location can act as a "global positioning system" for the robotic system, and its associated interventional tools to navigate in the magnetic resonance imaging system and human body. By interleaving with a real time MRI-scanned 3D roadmap, the MR tracking device enables accurate manipulation of the robotic device safely inside the human body.

Radiation sensitivity and positioning accuracy are partially dependent on the size and quality factor of the MR tracking marker. Generally, a single MR tracking marker is tracked from its proximate area (dependent upon the tracking marker radiation direction and radiation sensitivity) appearing as a "bright spot" in MRI image. A smaller proximate area will increase the tracking accuracy. Tuned tracking markers were conventionally mostly designed with a single layer structure. This design is disadvantageous because when applied with interventional instruments, a single layer structure design only utilizes a limited deployment area of the interventional tools in a 2D sense.

Furthermore, in conventional MR device/motion tracking with multiple wireless fiducial markers, it is always necessary to solve the peak-to-correspondence relationship between the MR tracking markers and marker signals, as back-projection of the tracker signal to the common output (e.g. the MRI scanner receive coil) would yield $N^3$ (N is the number of wireless fiducial makers) possible marker positions. Different approaches for this have been considered, such as arranging the markers with a fixed geometrical relationship, or utilizing the known geometrical layout and sensitivity of the MR receive coil array. However, the correspondence problem for multiple wireless fiducial markers remains a source of difficulty when the markers are not arranged in fixed geometrical layout, which hinders its implementation with flexible/non-rigid devices, such as a flexible catheter.

The invention is a wireless tracking marker with multilayer planar spiral inductors. The marker takes advantage of the mutual coupling effect between multiple layers of inductors to significantly improve the accumulated inductance within the same fill factor, thus offering a small form factor design while keeping a high sensitivity profile over its axial surface.

Further embodiments of the subject invention provide a sensor fusion method for determining and/or imaging the current positions of multiple MR tracking markers in a MR image with a dynamic/varying geometrical layout.

The term "multilayer" is used in this application for indicating that the MR tracking marker has a multilayer planar spiral structure such the radiation sensitivity can be significantly increased. The number of layers of the planar spiral structure is not relevant.

The present approach is mainly based on the use of multiple MR wireless markers with dynamic/varying relative positions, where determination of the correspondence between markers and marker signals relies on the position information feedback from a 3D shape sensor (e.g. FBG optic fiber).

An exemplary method for tracking the position and/or orientation of an object in a magnetic resonance (MR) imaging system includes the following steps: 1) attach a 3D shape sensor (e.g. FBG optic fiber) to the object of interest, and two or more of the MR wireless tracking markers relative positions are attached to the surface of the 3D shape sensor with a known geometrical layout; 2) provide one or more navigator tracking pulses in an MR pulse sequence; 3) receive the signals from the MR tracking markers via one or more MRI scanner receive coils, where the marker signals are responsive to the provided navigator tracking pulses; 4) determine a correspondence between the received marker signals and the markers such that each received marker signal corresponds to a particular marker. The real-time relative positions of the MR tracking markers and the 3D shape sensor measurements are required for this correspondence. This correspondence provides the position and/or orientation information of the object; and 5) provide the position and/or orientation information of the object as an input to another system for further processing.

The initial relative positions of the markers can be provided a priori (e.g., from the known dimensions and fixed marker locations on the 3D shape sensor). Alternatively, the relative positions of the markers can be provided by performing a preliminary scan of the markers that have been attached to the 3D shape sensor. For example, the marker positions can be found by using multiple back projections from the preliminary scans. Alternatively, an image-based acquisition and reconstruction can be performed in this preliminary scan, followed by morphological image processing, in order to determine the markers geometrical layout.

Additionally, knowledge of the marker positions obtained from the preliminary scans can be used to optimize the number and/or the orientation of navigator tracking pulses to be used during the actual scan for tracking the object. For example, projections can be selected to maximize marker signal peak separation.

Use of the wireless tracking marker does not depend critically on details of the navigator tracking pulses. Suitable navigator tracking pulses include, but are not limited to: gradient echo pulses, spin echo pulses, free induction decay pulses, zero echo time pulses, and pulses having an echo time of 1 ms or less.

BRIEF DESCRIPTION OF THE DRAWINGS

FIG. 7 is an illustration of the peak-to-correspondence problem with multiple wireless tracking markers.

FIG. 17 is a chart of the design specifications of a multilayer inductor.

FIG. 20a shows a cross-sectional view of the device of FIG. 19 while FIG. 20b shows a top view of the device of FIG. 19.

FIG. 21a show an individual marker of the device of FIG. 19 while

DETAILED DESCRIPTION

Figure 1A:
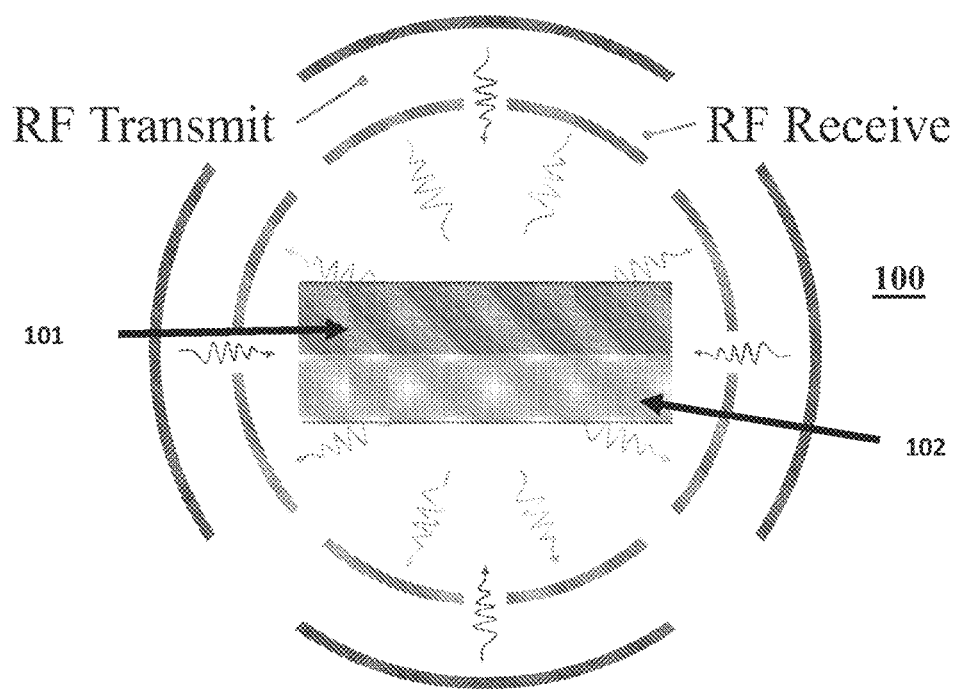
FIG. 1a is a diagram of a wireless tracking marker inductively coupled with an MRI receiver coil.

Embodiments of the subject invention provide an MR tracking device designed with a multilayer structure, (including but not limited to planar spiral inductor, planar parallel plate capacitor) that enhances electrical performance and physical compactness of a tracking device. The planar spiral inductor can be either a flat or rounded form, and include vias that connect different layers together to form a closed circuit. In particular, the multilayer structure can greatly enhance the inductance of the inductor by introducing mutual inductance between different layers (e.g. for a 4 layer planar inductor the total inductance will be the summation of 4 self-inductance and all mutual inductance induced between every layer). The MR marker can be composed of non-ferromagnetic materials to ensure compliance with an MRI machine.

Multiple parallel plate capacitors can be formed by utilizing a multilayer structure to increase the total capacitance. The planar spiral inductor and the parallel plate capacitor can be connected with a photodiode/photoresistor used as a "optical switch" to alter the electrical characteristics of the MR tracking device, e.g. by illuminating light on the optical component, the MR tracking device will exhibit a particular resonant frequency $f_1$, and by turning off the light the MR tracking device will exhibit another resonant frequency $f_2$.

The electrical characteristics of the MR tracking device (i.e. inductance, capacitance, and resistance) can be calculated by either Finite Element Analysis (FEA) or an analytical method. With FEA, a 3D volumetric model of the MR tracking device is generated for creation of an initial mesh, which can be in the form of tetrahedron/bricks/prism/pyramids etc. A full-wave field solver can be used to calculate the radio-frequency scattering parameter of the MR tracking device, and the result can be saved to a data base. An optimal performance is ensured by performing parametric analysis on the size/shape/materials of the MR tracking device. Another method is to use analytical approximation to compute the electrical characteristics. Several methods can be adopted, e.g. the Greenhouse method provides an analytical method for calculating the inductances of planar thin or thick film coils. An estimation for calculating multiple layers parallel coil inductances can be derived from these equations to provide an approximate inductance as the starting point for coil design optimization. The Greenhouse method can be applied as a computer script/program to automatically calculate inductance based on the coil parameters.

During the operation of an MRI scanner with magnetic field strength $B_0$, citation pulse emitted from the $B_1$ field leads the nuclear spin of hydrogen nuclei (protons) to be deflected from their equilibrium precession along the main $B_0$ field to a flip angle $\alpha$. When the hydrogen spin returns to the lower energy state, the RF receiver coil of the MRI machine measures an echo signal. Generally, the signal intensity is maximal at a flip angle of 90°.

Figure 1B:
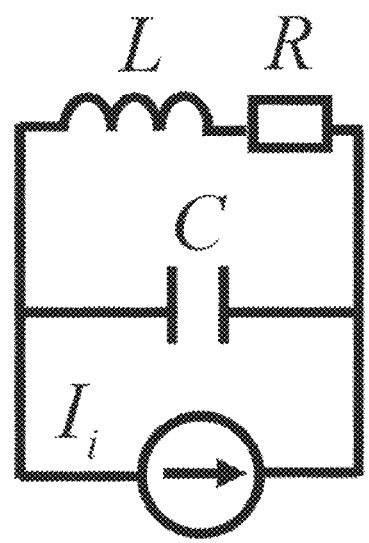
FIG. 1b a schematic diagram of an inductively couple RF coil circuit.

The wireless MR tracking marker works by an inductive coupling approach to the receiver coil of the MRI scanner, and provides a local signal enhancement at the proximity that contains hydrogen nuclei $^1$H atom, as shown in FIG. 1. The MRI tracking marker with inductance L, capacitance C, and resistance R should resonate at the Larmor frequency of the working MRI machine, which is defined by:

$$f_{Larmor} = \frac{\gamma}{2\pi} B_0 \qquad (0)$$

where $\gamma/2\pi$=42.58 MHz/T is the gyromagnetic ratio of the hydrogen nuclei $^1$H atom. RF transmit mode and RF receive mode happen sequentially during operation. In RF transmit mode, a MR pulse sequence with low flip angle excitation can be applied. The MR transmit coil with flux $\phi_{B1}$ initially couples with the resonant circuit at the Larmor frequency and an RF current $I_{induced}$ is induced in the circuit. The induced current $I_{induced}$ generates a linearly polarized magnetic field at the center of the inductor locally resulting in a flux $\phi_{marker}$:

$$\phi_{marker} = -iQ_{marker}\phi_{B1} \qquad (2)$$

where $Q_{marker}$ is the quality factor defined by:

$$Q_{marker} = \frac{1}{R}\sqrt{\frac{L}{C}} = \frac{2\pi f_{Larmor} L}{R} \qquad (3)$$

The additional flux from the resonant circuit is added to the original flux $\phi_{B1}$ from the RF coil, thus introduced in an additional excitation field that amplifies the flip angle of the surrounding spins. The amplified signal is dependent on the quality factor $Q_{marker}$ of the resonant circuit, and the orientation of the inductor with respect to the RF field $B_1$. Since other regions are not affected, the positive local contrast between the MR tracking coil and background can be differentiated. In RF receive mode, the MR tracking coil picks up the MR signal in its proximity, resulting in a local linearly polarized magnetic flux that can be inductively coupled to the MRI RF receive coil. Thus, at the measurement phase, the total magnetic flux measured is doubled.

Although several closed-form equations have been proposed in literature to approximate the inductance of planar spiral coil, there is no readily available expression for multilayer rectangular planar spiral coils since the flexible winding structure can have an irregular geometry. To analyze the inductance of the coil design, the Greenhouse method can be adopted to develop approximation for multilayer inductance. The Greenhouse method approximates the inductance of an arbitrary coil by partitioning it into a set of independent straight conductors. The total inductance is computed by summing the self-inductance of each conductor and mutual inductance between every two parallel conductors.

The exact self-inductance for a straight conductor can be calculated as follows:

$$L = 0.002l\left\{\ln\left(\frac{2l}{GMD_{self}}\right) - 1.25 + \frac{AMD_{self}}{l} + \left(\frac{\mu}{4}\right)T\right\} \quad (4)$$

where l is the segment length, $GMD_{self}$ and $AMD_{self}$ are the self-geometric and arithmetic mean distances, respectively, μ is the conductor permeability, and T is the frequency correction parameter. All length values can be calculated in cm.

To calculate the self-inductance of a conductor, the $GMD_{self}$ of the conductor cross-section is used by treating the conductor as an infinite number of parallel filaments. The conductor's self-inductance is equal to the sum of the mutual inductances of each filament pair, with the distance between them is taken as the $GMD_{self}$. For a rectangular cross section with thickness t→0 the $GMD_{self}$ is 0.22313(w+t), where w is the width of the conductor cross-section.

For a thin-film conductor, the $AMD_{self}$ can be approximated to the straight-line condition t→0, which states that the $AMD_{self}$ equals ⅓. Assuming the near-direct-current condition, T=1, and that the conductor has magnetic permeability of 1, the equation for self-inductance of a thin-film conductor with rectangular cross section is derived from (4) to be:

$$L = 0.0021\left\{\ln\left[\frac{2l}{w+t}\right] + 0.50049 + \left[\frac{w+t}{3l}\right]\right\} \quad (5)$$

For a rectangular thin-film inductor, only parallel segments contribute to the total inductance of the coil as mutual inductance. If the direction of current in both segments is the same, then the mutual inductance is positive, and if they are in opposite directions, the mutual inductance is negative. The mutual inductance between two parallel segments can be expressed as:

$$M = 2lP \quad (6)$$

where M is the mutual inductance in nanohenries, and P is the mutual inductance parameter, calculated by:

$$P = \ln\left\{\frac{l}{GMD} + \left[1 + \frac{l^2}{GMD^2}\right]^{\frac{1}{2}}\right\} - \left[1 + \frac{GMD^2}{l^2}\right]^{\frac{1}{2}} + \frac{GMD}{l} \quad (7)$$

When calculating P, the length l is determined by the subscript of P, and GMD is taken between the two conductors. The approximate value of the GMD is calculated from the equation:

$$GMD = d - \exp \quad (8)$$

$$\left\{\frac{1}{12}\left(\frac{d}{w}\right)^2 + \frac{1}{60}\left(\frac{d}{w}\right)^4 + \frac{1}{168}\left(\frac{d}{w}\right)^6 + \frac{1}{360}\left(\frac{d}{w}\right)^8 + \frac{1}{660}\left(\frac{d}{w}\right)^{10} + K\right\}$$

where d is the distance between the segment centers. For multilayer inductors, d is taken as the Euclidian distance between the segment centers.

For two parallel conductor segments, i and k, the total mutual inductance between them is:

$$2M_{i,k} = (M_{k+m} + M_{k+n}) - (M_m + M_n) \quad (9)$$

where $M_i$ is the mutual inductance between two parallel conductors with the same length. The subscript of the mutual inductance variable M is used in its calculation. Using $M_{k+m}$ for example:

$$M_{k+m} = 2l_{k+m}P_{k+m} = 2(k+m)P_{k+m} \quad (10)$$

Note that the length l is also used in calculating P, as shown in equation (7). For the case where the two segments are aligned symmetrically, i.e. n=m, the equation can be simplified to:

$$2M_{i,k} = 2M_{k+n} - 2M_n \quad (11)$$

Equation 11 is an exact equation for all conductor pairs except those using segment 1 and any segments not shortened incrementally (according to the conductor width and spacing of parallel segments). For non-symmetrical cases, using the symmetrical formula introduces little error, and because the same asymmetry exists in the negative inductance calculations, the error is mostly compensated.

Equations (4)-(10) can be used to calculate the inductance of a single layer inductor, and are extended to calculating inductance for multiple identical layers. To calculate mutual inductance between two different layers, the distance d, in equation (8) is taken as the straight-line distance between the segment centers. The total inductance of each individual layer is treated to be equal to the total inductance of a single layer inductor of the same dimensions. Therefore, the total inductance of a multilayer inductor is taken as the sum of the total inductance of every layer and the mutual inductance between each layer. Therefore, for a coil with N layers, the total inductance can be expressed as:

$$L_{Total} = \sum_{i=1}^{N} L_i + \sum_{i=1}^{N} \sum_{j=1, j\neq i}^{N} M_{ij} \quad (12)$$

The DC resistance of the tracking marker can approximated with the specification of the length of the conductive trace $l_c$, resistivity of the conductive material $\rho_c$, the conductive trace thickness $t_0$, and the trace thickness w.

$$R_{DC} = \frac{\rho_c \cdot l_c}{w \cdot t_0} \quad (13)$$

Since the tracking marker is operating at 1.5 T Larmor frequency, the current induced during inductive coupling tends to flow on the conductor surface, and the uneven current distribution leads to a decrease in the effective conductor cross-sectional area. The approximation of the marker resistance can be further extended by taking skin depth into consideration, $$\delta = \sqrt{\frac{2 \cdot \rho_c}{2\pi \cdot f_{Larmor} \cdot \mu}} \quad (14)$$

By incorporating the skin depth into (13), the resulting AC resistance $R_{AC}$ can be approximated as:

$$R_{AC} = \rho_c \cdot l_c \cdot \left(\frac{1}{w \cdot t} + \frac{1}{2\delta(w+t)}\right) \quad (15)$$

Thus, the quality factor of the tracking marker can be approximated. Note that as the amplified signal from the tracking marker is dependent on the quality factor, it is desirable to reduce the resistance of the copper trace, which is feasible by using another material with higher conductivity $\rho_c$ or by increasing trace thickness w.

The MR tracking device can be fabricated either "on-site" or "off-site". The MR tracking device can be fabricated "on-site" with multi-material additive fabrication on the surface/cavity of the MRI-guided robotic system and its associated tools. The process can be divided into several steps, first a fundamental layer can be deposited on the surface/cavity of said systems and tools. Second, the conductive layer can be inkjet-printed on the fundamental layer to create the conductors for the passive electronic component (e.g. planar spiral inductor, parallel plate capacitor). The first and second step can be repeated more than once to create a multilayer structure to improve the device's compactness. Finally, a biocompatible and MR-compatible material is deposited on the fabricated structure for encapsulation.

The MR tracking device can be fabricated "off-site" with flexible electronics (e.g. flexible printed-circuit board). The process includes the assembling of electronic circuits on flexible plastic substrates (e.g. polyimide, PEEK, or other conductive polyester film), and the conductor can be screen printed silver and copper. The flexible printed circuit can be made with photolithographic technology, or lamination of thin copper strips between layers of polymer. By using flexible printed circuit boards to fabricate the MR tracking device, it ensures a tightly assembled electronics package.

FIG. 1 is a diagram of a wireless tracking marker 100 comprising a first conductive planar coil 101 and a second conductive planar coil 102; the marker inductively coupled with an MRI receiver coil. The signal source can be body tissue/fluid, or any materials with hydrogen atoms.

Figure 2A:
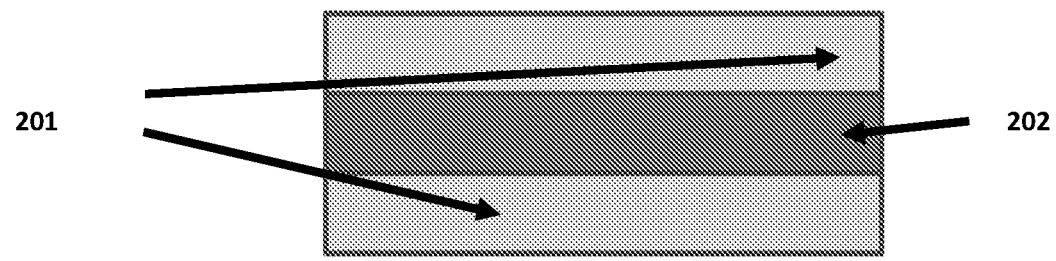
FIG. 2a is a diagram of a flexible printed circuit (FPC).
Figure 2B:
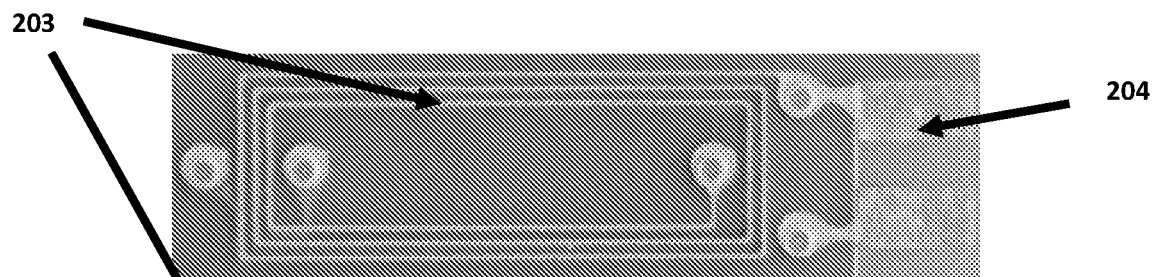
FIG. 2b is an image of an MR tracking marker with a soldering joint left for surface mount components (e.g. SMD capacitor).
Figure 2C:
FIG. 2c is an image of an MR tracking marker using its layers as a parallel plate capacitor.

FIG. 2a is a diagram of a flexible printed circuit (FPC) with two copper plates 201 disposed on a top surface and bottom surface of an interlayer 202. As seen in FIGS. 2b and 2c, an "off-site" MR tracking device can be fabricated as following manner. Two double layer flexible printed circuit (FPC) sheets can be made separately. On each double layer FPC sheet, copper tracks 203 can be printed on the opposite sides of a polyimide substrate 202, and the two layers can be electrically connected in series via a conductive hole plated-through the polyimide substrate 202. The MR tracking marker can be designed in two forms. An MR tracking marker can include a soldering joint 204 for surface mount components (e.g. SMD capacitor). Another form of the MR tracking marker uses its FPC layers as a parallel plate capacitor 205. In addition to polyimides, the substrate can comprise PEEK or other conductive polyester film. On top of the copper layer, a thin coverlay can be further overlaid to provide insulation prior to bonding the two FPC sheets with a thin layer of epoxy in order to from a multilayered coil.

Figure 3:
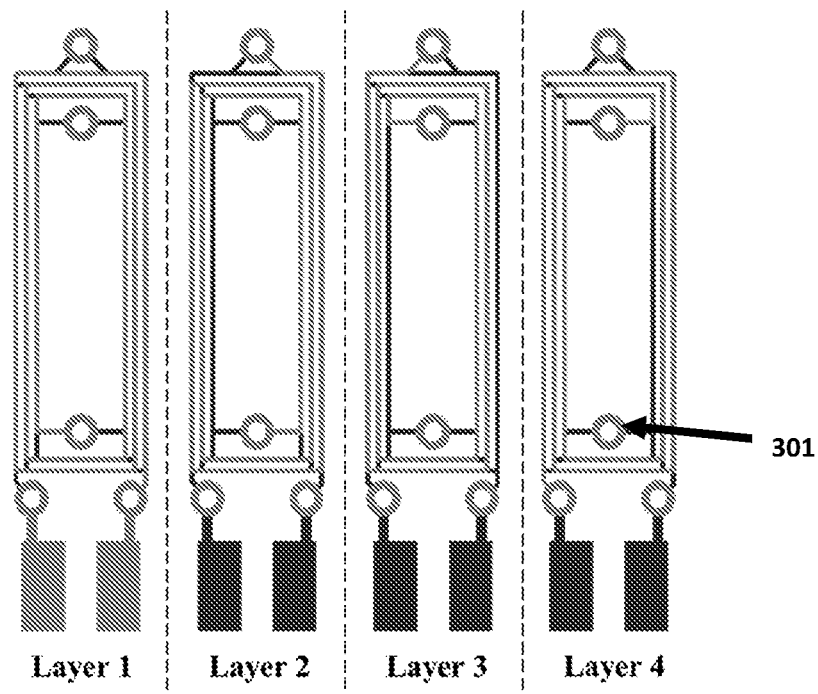
FIG. 3 is a diagram of a multilayer design of an MR tracking coil. The orange rectangular traces represent the copper conductor, and the hollow circles are the inter layer via.
Figure 4:
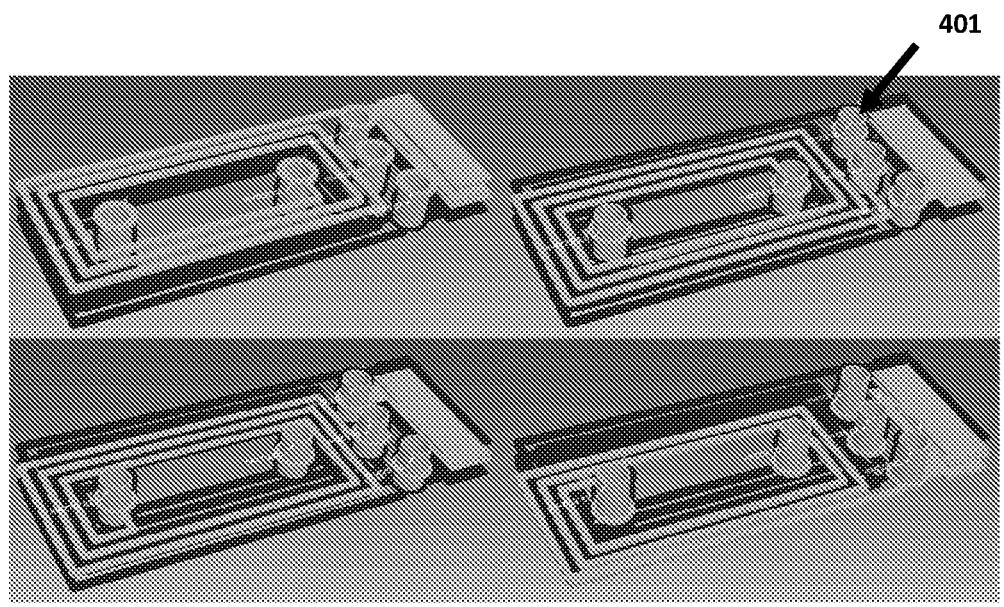
FIG. 4 is an alternative via arrangement for a 4 layer design of an MR tracking coil.

FIG. 3 is a diagram of a four layer design of an MR tracking marker. Multiple vias 301 that penetrate through all layers can be utilized to connect the conductors on different layers. FIG. 4 is an alternative design of the MR tracking coil with a different via 401 arrangement for the 4 layer design of the MR tracking coil.

Figure 5:
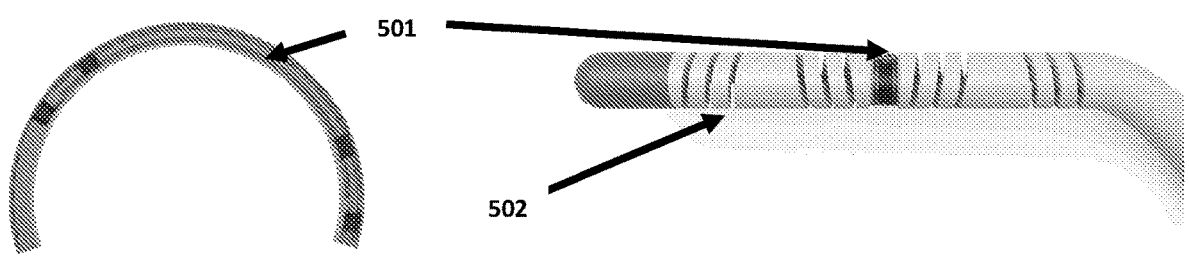
FIG. 5 is a diagram illustrating that the tracking marker is bendable and can be attached to a curved surface.
Figure 6:
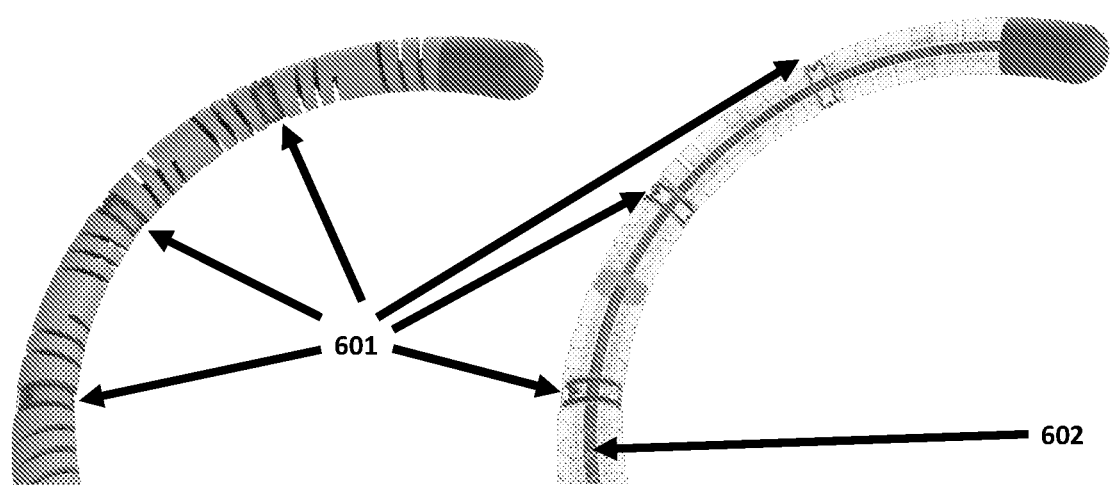
FIG. 6 is an illustration of 3 wireless tracking markers mounted on the surface of a flexible catheter, with an embedded 3D shape sensor

As seen in FIG. 5, the MR tracking marker 501 is bendable and can be attached to a curved surface, for example to a bendable catheter 502. As seen in FIG. 6, 3 wireless tracking markers 601 are mounted on the surface of a flexible catheter, with an embedded 3D shape sensor, for example Fiber Bragg Grating (FBG) optic fiber 602.

Figure 8:
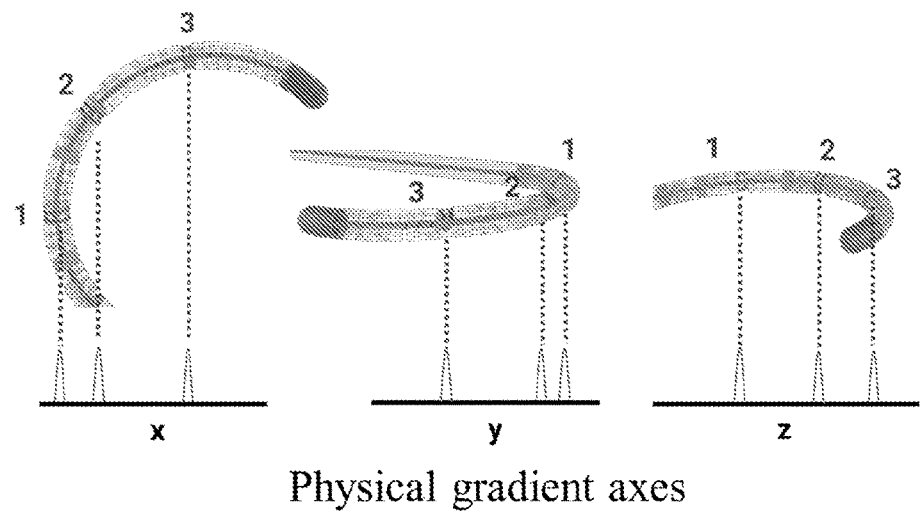
FIG. 8 is a diagram illustrating that with 3D shape information obtained from the FBG optic fiber, the peak-to-correspondence problem can be solved with the obtained geometrical layout from the FBG optic fiber
Figure 9:
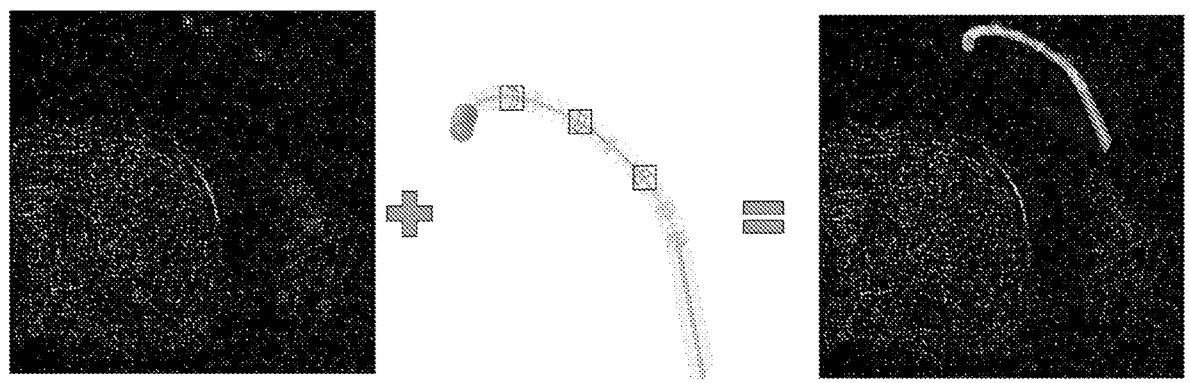
FIG. 9 shows images illustrating that multiple MR tracking marker positions can be overlaid on an MR image.

As illustrated by FIG. 7, in conventional MR device/motion tracking devices with multiple wireless fiducial markers the peak-to-correspondence relationship between the MR tracking markers and marker signals creates challenges. With 3D shape information obtained from the FBG optic fiber, the peak-to-correspondence problem can be solved with the obtained geometrical layout from the FBG optic fiber, as seen in FIG. 8. FIG. 9 shows multiple MR tracking marker positions can be overlaid on an MR image.

Figure 10A:
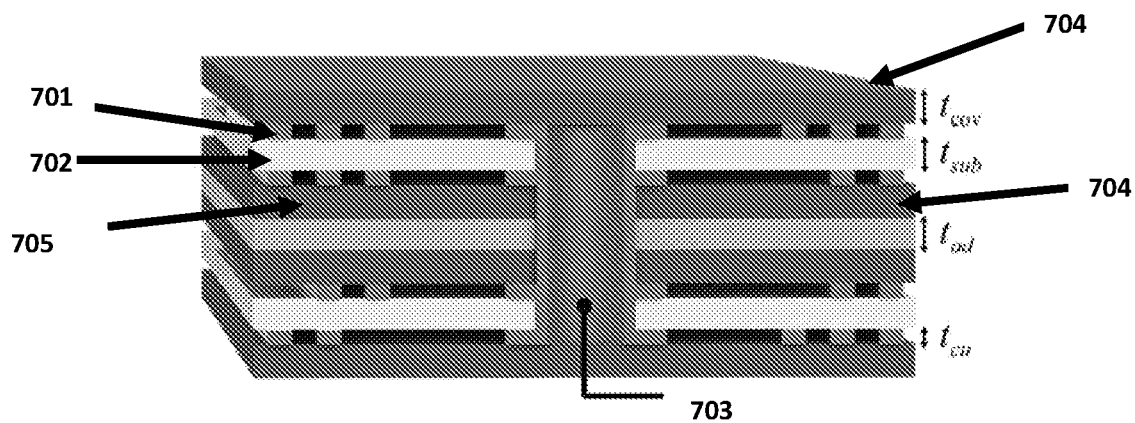
FIG. 10a shows a diagram of a multilayer fabrication structure of a MR tracking coil.
Figure 10B:
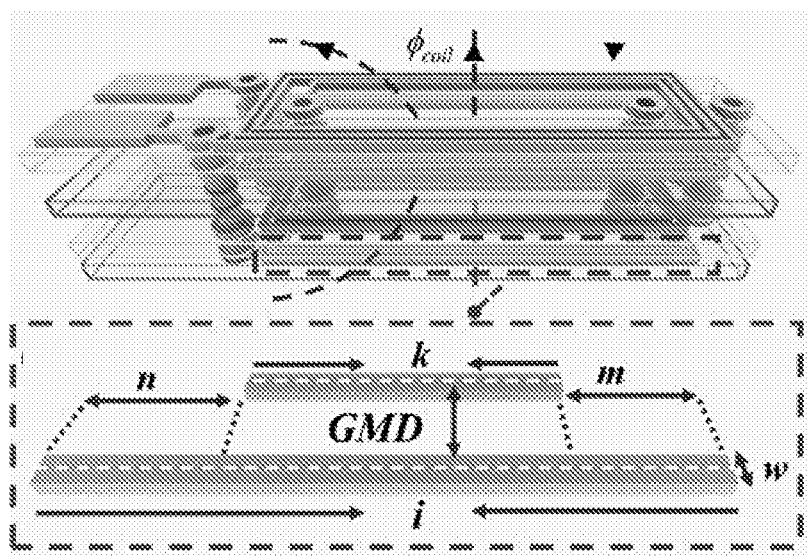
FIG. 10b shows a diagram illustration the definition of geometric mean distance (GMD).

FIG. 10a is a diagram of a multi layered coil, in which two double layer flexible printed circuit (FPC) sheets are bonded together. Copper tracks 701 can be printed on the opposite sides of a polyimide substrate 702, and the two layers can be electrically connected in by a via 703 made from conductive material and penetrating both flexible prints sheets. A coverlay 704 can be applied to provide insulation prior to bonding the two FPC sheets with an adhesive 705. FIG. 10(b) shows a diagram illustration the definition of geometric mean distance (GMD) for the coil of FIG. 10(a).

Figure 11A:
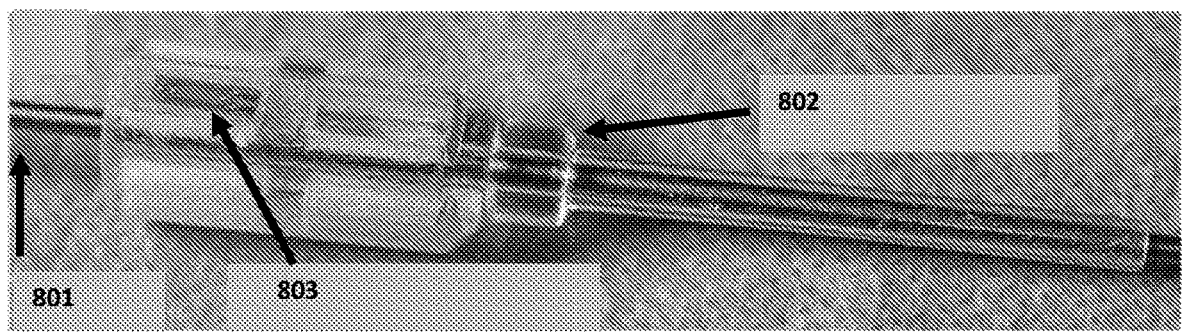
FIG. 11a is an image of a needle guide embedded with two MR tracking markers (only one marker is shown).
Figure 11B:
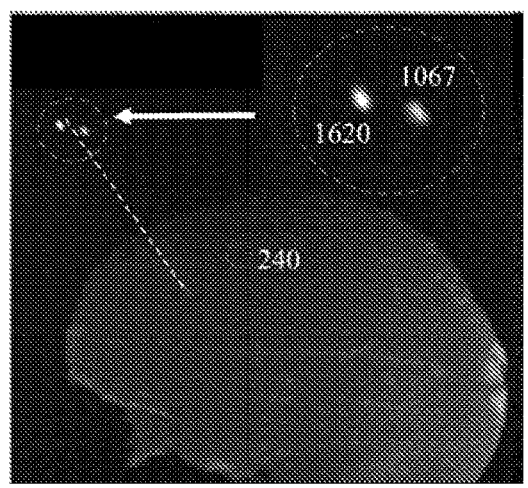
FIG. 11b is a MR image of a brain phantom made with agar gel, with the two tracking markers are shown as bright spots.
Figure 11C:
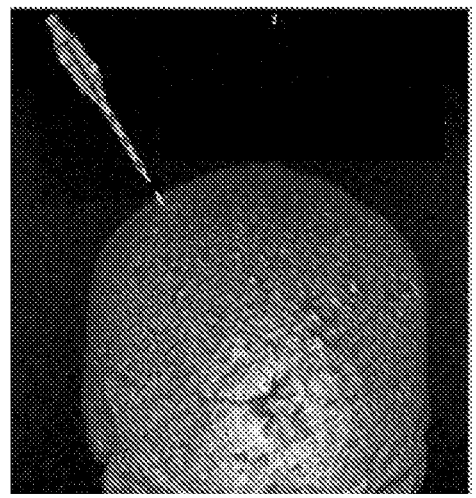
FIG. 11c shows a virtual augmentation image of the markers posed on top of the 3D reconstructed brain phantom.
Figure 11D:
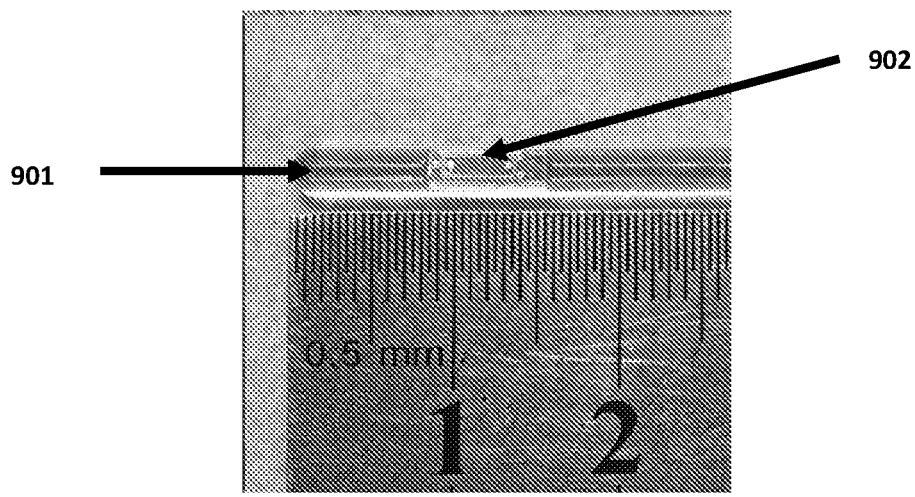
FIG. 11d is an image of a 3D-printed 3 mm catheter embedded with a tracking marker.

FIG. 11(a) is an image of a needle 801 within a needle guide 802, which has been embedded with two MR tracking markers 803 (only one marker is visible). FIG. 11(b) is an MR image of a brain phantom made with agar gel, with the two tracking markers shown as bright spots. It can be observed that at a low flip angle, the intensity signal between the marker and the brain phantom has a significant difference. FIG. 11(c) shows a virtual augmentation image of the markers posed on top of the 3D reconstructed brain phantom. FIG. 11d shows a 3D-printed 3 mm catheter 901 embedded with a tracking marker 902. The small form factor enables a simple development of new interventional tools.

Figure 12:
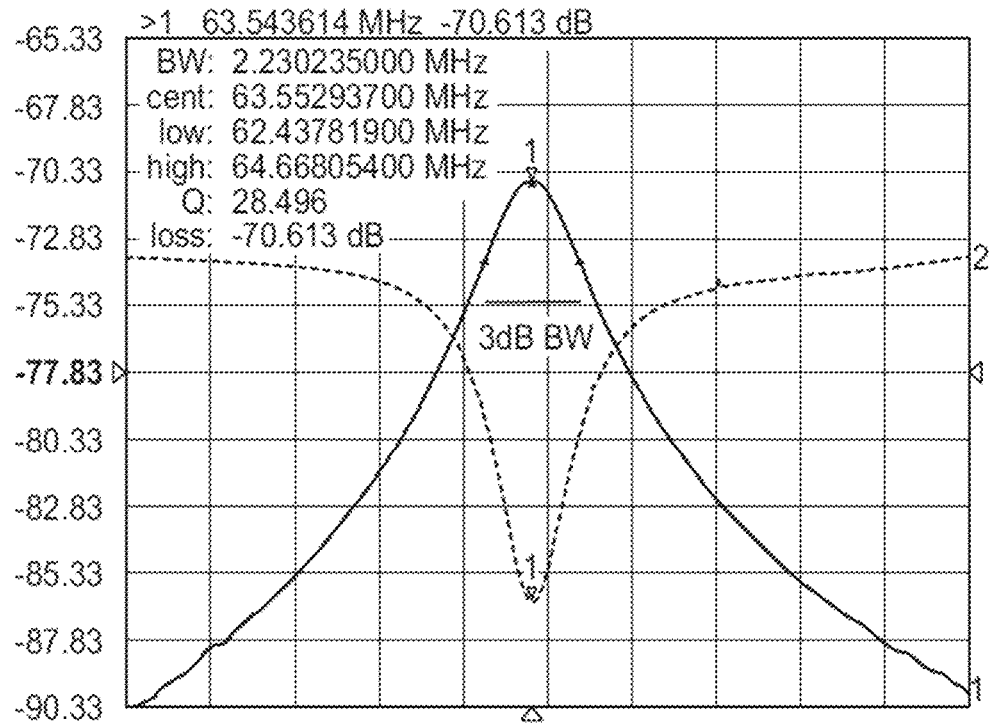
FIG. 12 is a plot of the scattering measurement of a tracking marker integrated on the 3D-printed catheter and shows a quality factor measurement with a 3 dB bandwidth.

FIG. 12 is a plot of the scattering measurement of a tracking marker integrated on the 3D-printed catheter and shows a quality factor measurement with a 3 dB bandwidth.

Figure 13A:
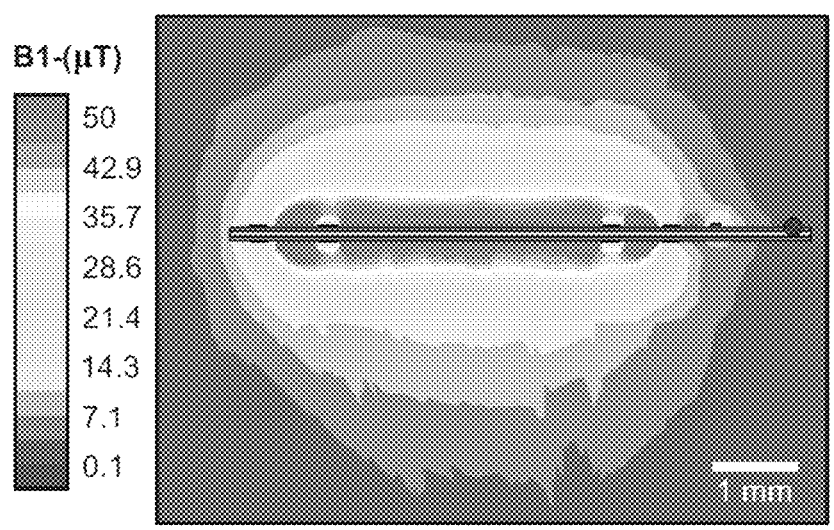
FIG. 13a is an EM field simulation of a sagittal view of the tracking marker.
Figure 13B:
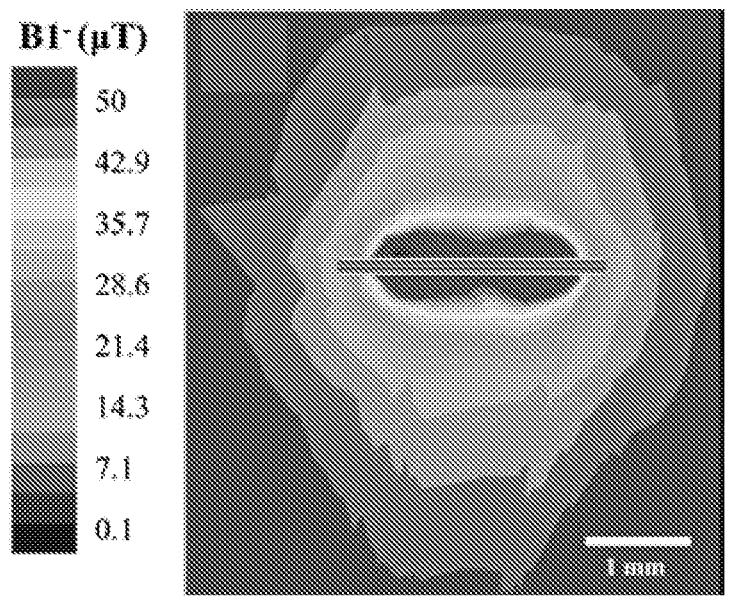
FIG. 13b is an EM field simulation of an axial view of the $B_1^-$B1-EM field simulation with the MR tracking marker.
Figure 13C:
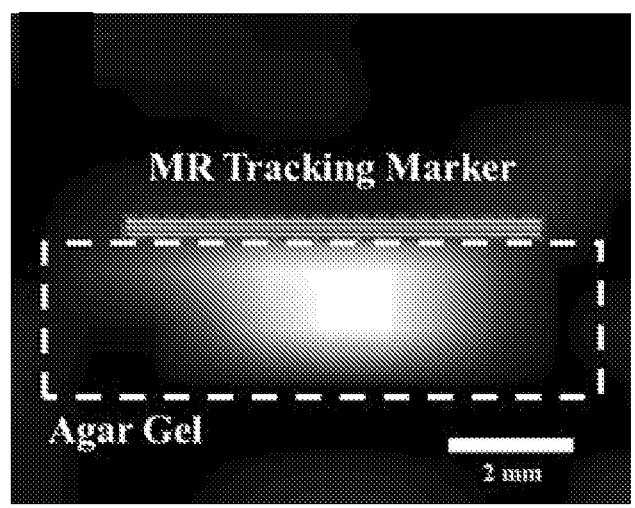
FIG. 13c is a high resolution MR image of a tracking marker mounted on a 3D-printed plastic block embedded with agar gel phantom, acquired with a gradient echo (GRE) sequence.

FIG. 13a is an EM field simulation of a sagittal view (cross-section of the tracking marker). FIG. 13b is an EM field simulation of an axial view of the $B_1^-$B1-EM field simulation with the MR tracking marker. FIG. 13c is a high resolution MR image of a tracking marker mounted on a 3D-printed plastic block embedded with agar gel phantom, acquired with a gradient echo (GRE) sequence. The imaging slice was oriented in the sagittal plane along the MR tracking marker.

Figure 14:
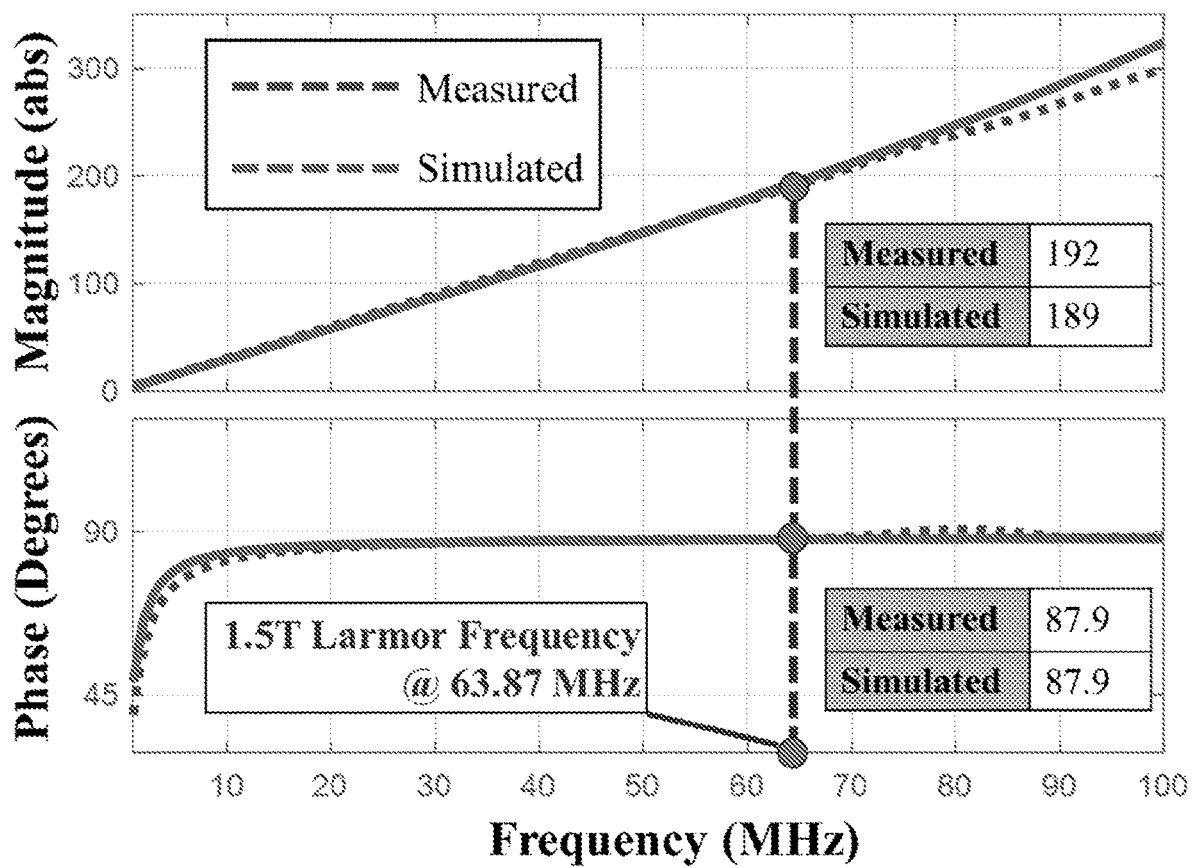
FIG. 14 is a plot of the measured and finite element model (FEM) simulated impedance of the multilayer planar spiral inductor.

FIG. 14 is a plot of the measured and FEM simulated impedance of the multilayer planar spiral inductor. The results show good correspondence from 1 to 100 MHz. The vertical dashed line indicates the 1.5 T Larmor Frequency.

Figure 15A:
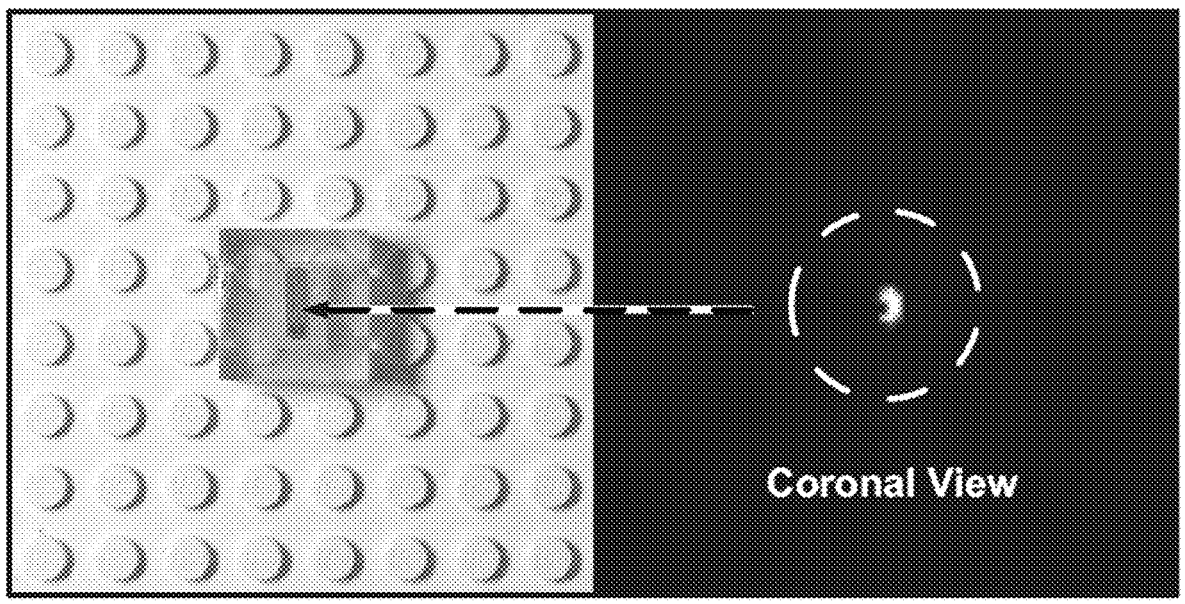
FIG. 15a is an image of the left of a wireless tracking marker mounted on a 3D-printed block filled with agar gel and an MR image on the right with a bright spot representing the proximate $^1$H atoms with and amplified signal.
Figure 15B:
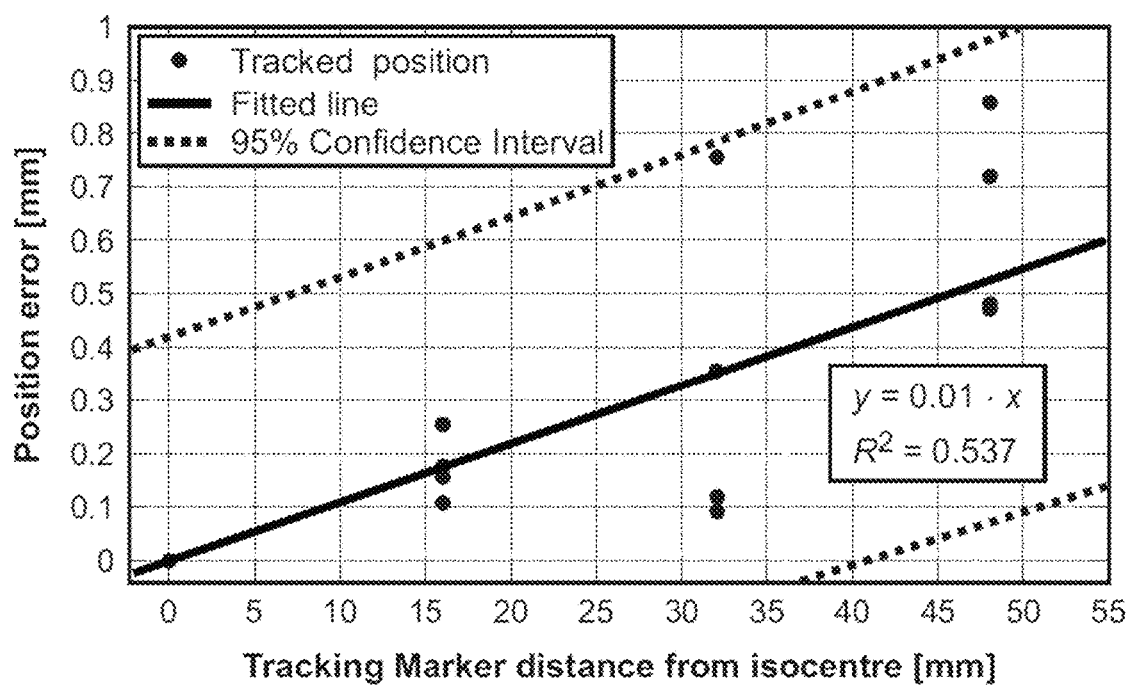
FIG. 15b is a plot of the calculated 2D position error of the tracking marker against its distance from the isocenter.

FIG. 15a is an image of the left of a wireless tracking marker mounted on a 3D-printed block filled with agar gel and an MR image on the right with a bright spot representing the proximate $^1$H atoms with and amplified signal. FIG. 15b is a plot of the calculated 3D position error of the tracking marker against its distance from the isocenter. The data was fitted with a solid line that intercepts at zero point. The short-dashed lines indicate the 95% confidence interval.

Figure 16:
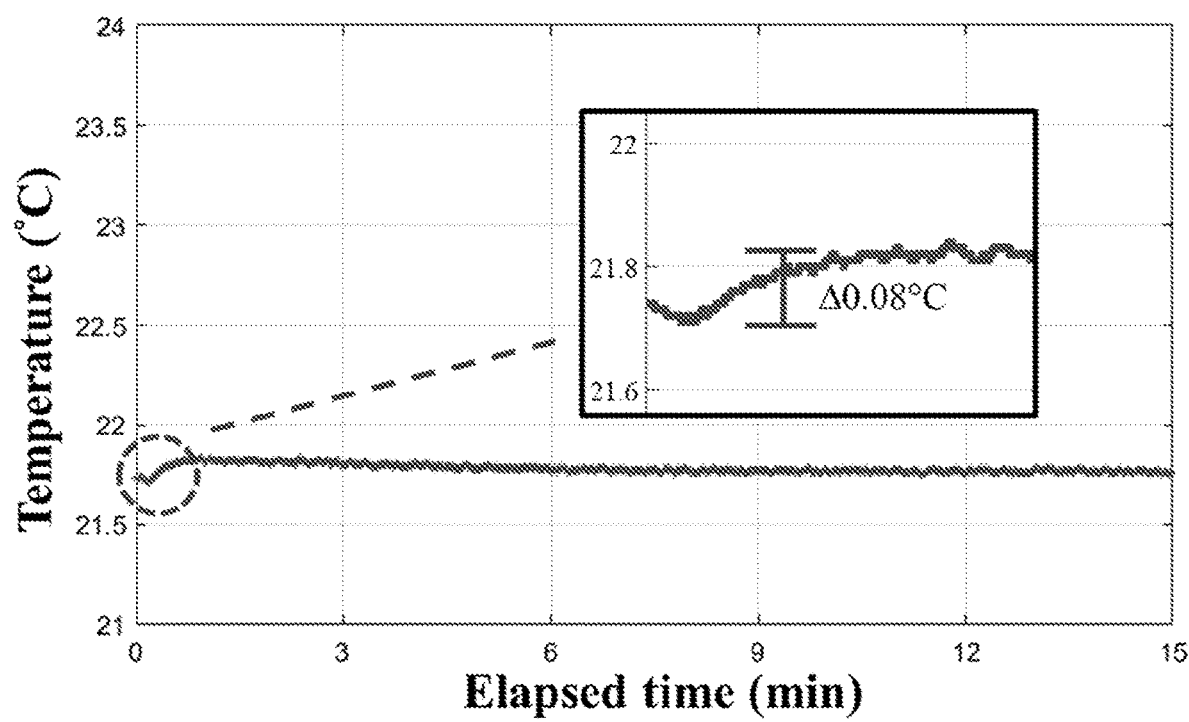
FIG. 16 is a plot of the temperature measurement of the MR tracking marker over a 15 min FSE.

FIG. 16 is a plot of the temperature measurement of the MR tracking marker over a 15 min FSE. The temperature probe of the optical thermometer was directly attached to the multilayer inductor L of the tracking marker. FIG. 17 is a chart of example design specifications of a multilayer inductor.

The MR tracking device can be incorporated into an MR-guided robotic system in two different perspectives, robotic kinematic control of the MR-guided robotic system, and positional information overlay on a human-machine interface.

The MR tracking device enables the geometrical location of the MRI-guided robotic system and its associated intervention tools to be tracked in real time. The positional information can be feedback to the robotic control system to form a close-loop position controller to offer manipulation with higher accuracy, precision, and robustness. The kinematic control of the robotic system is not only important for precise control, but also for ensuring safe manipulation in practical operation.

The MR Tracking device enables the geometrical position of the MRI-guided system to be shown in a human-machine interface. The information can be visually overlaid on the real-time scanned MR image, thus providing an intuitive visualization between the body tissue and the robotic system's body and the interventional tool.

The MRI pulse sequence enables fast imaging technique to depict the anatomy inside body for specific prescription through human-machine interface. The signals are acquired using multi-channel coil with multiple receivers, which can enable parallel imaging to further reduce the total scan time. The reconstructed images from MRI scanner embedded with physical coordinates are sent to human-machine interface for real-time visualization and overlaying the positions of tracking coils, thereby allowing user to define the target position and monitor the needle position.

Figure 19:
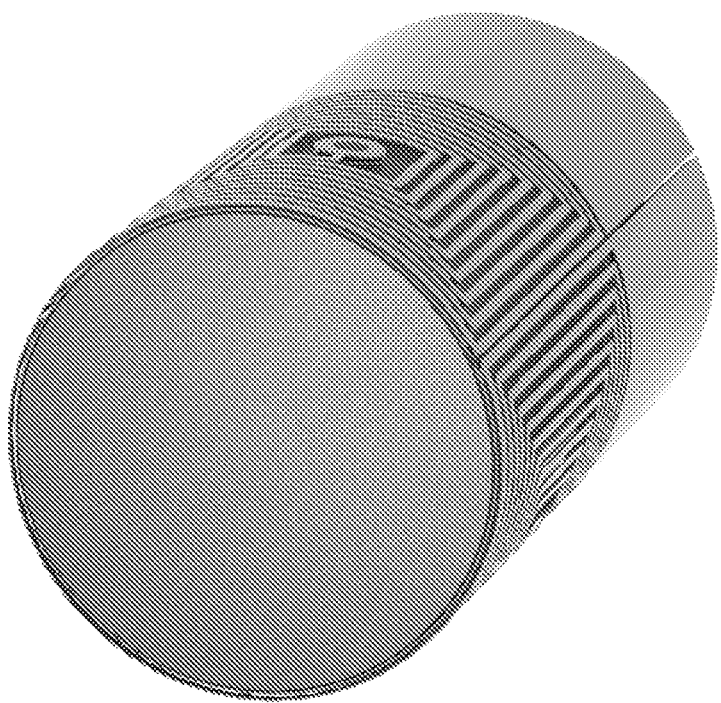
FIG. 19 depicts an omnidirectional tracking device with three curved resonant circuits evenly wrapped on a cylindrical substrate (e.g., catheter).

In another aspect, the present invention uses planar spiral coils in omnidirectional position sensing. In this embodiment, three or more markers are applied to provide 3D positional tracking with negligible dependency on orientation as depicted in FIG. 19. The following discussion relates to the orientation issues faced by markers in an MRI scanner.

Figure 18:
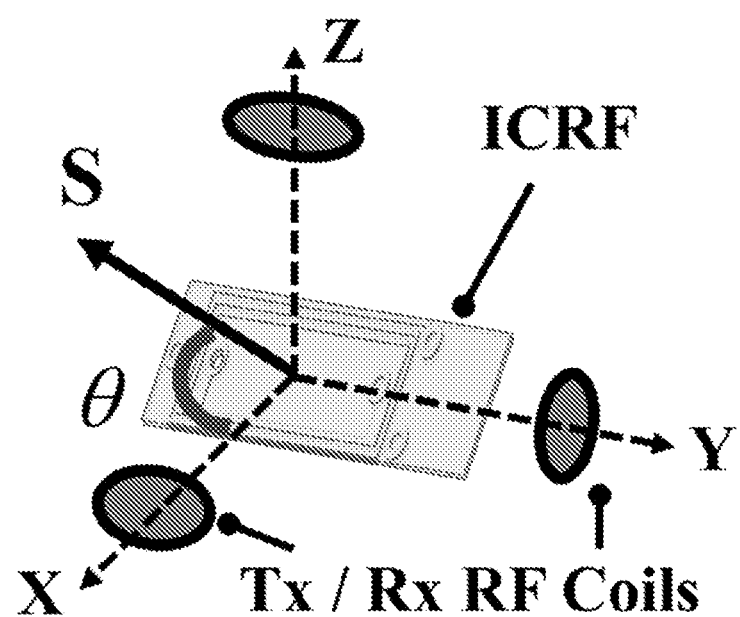
FIG. 18 depicts the geometrical relationship between an inductively-coupled radio frequency (ICRF) coil with MRI RF transmit and receive coils.

In transmit mode, the RF transmitter coil of a MR scanner emits a circularly polarized field $B_1^+$ from two orthogonal channels, with two components $B_{1,x}$ and $B_{1,y}$ that has equal magnitude but 90° phase difference. The $B_1^+$ field rotates the net magnetization away from $B_0$ at a flip angle α. When the $B_1^+$ field passes through the marker, it induces a linearly polarized magnetic flux $\phi_m$ at the inductor component, resulting in an induced current $I_i$.

$$\phi_m = -iQ_m B_1^+ \cdot AS$$

where $Q_m$ the quality factor of marker circuit, A is the marker's inductor surface area, and S is the surface normal vector. The additional flux from the marker amplifies the flip angle α of surrounding spin. Sequentially, in RF receive mode, MR signal from marker's surrounding spin also generates a linearly polarized magnetic flux at the inductor that can be inductively coupled to the MRI RF receive coil. Therefore, at the measurement phase, the total magnetic flux generated at the marker is $2\phi_m$. This additional magnetic flux leads to a well-differentiated area of positive contrast defined by the RF sensitivity profile of the marker. When the tracking marker is placed inside the scanner, only the $B_1^+$ and $B_1^-$ component that is parallel to marker's surface normal vector S is effective to generate current through its inductor. Refer to FIG. 18 when S is on the X-Y plane, theoretically the signal is constant as the effective flux passing through the marker surface is the same. But when the surface normal vector S is on the X-Z plane with an angle θ from x-axis, the effective flux becomes $$\phi_m = -iQ_m B_1^+ \cdot A \cos(\theta)$$

When θ=90°, the effective $B_1^+$ field becomes zero and no signal enhancement can be achieved.

FIG. 19 depicts the omnidirectional tracking marker design with three curved resonant circuits evenly wrapped on a 3 mm diameter catheter surface, such that the circuits 3 surface normal vectors $S_{1-3}$ share the same centroid and are separated by 120° alternatively on same plane. Note that although three markers create the device of FIG. 19, other odd numbers greater than three may be used (e.g., 5, 7, 9).

To prove sensitivity along 3 axes, the surface integral of the $B_1$ field with the curved surface is developed.

$$\Phi_B = \oiint_A B \cdot dA$$

$$\Phi_B = \oiint_A B \cdot n \, dA$$

Put the B1 field as $$B = \cos\theta x + \sin\theta y$$

$$D = \sqrt{3} R$$

$$A = \sqrt{3} LR$$

1. Axial Axis //Z

Flux integral on marker 1 for theta from 0 to 360

$$\Phi_B = \int_0^{360} (\cos\theta x + \sin\theta y) \cdot (\sqrt{3} LR x)$$

$$\Phi_B = 2\sqrt{3} LR$$

$$\Phi_B = 3.46 LR$$

Total flux integral=individual*3

2. Axial Axis //X and //Y $$\Phi_B = \int_0^{360} (\cos\theta x + \sin\theta y) \cdot (1.5 LR y)$$

$$\Phi_B = 3 LR$$

As a result, the signal sensitivity is more or less the same in all directions. By principle of reciprocity, the flux integral is approximately doubled in the receive mode.

Monolithic FPC Curved Marker

Figure 21A:
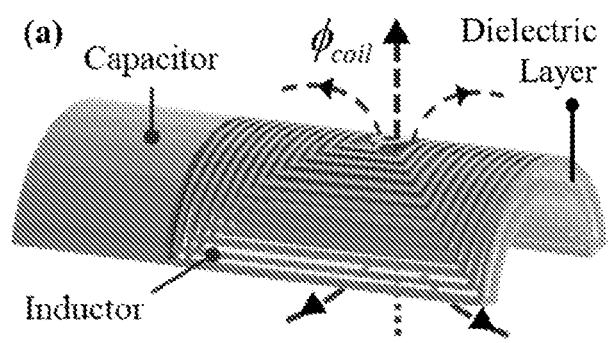
Figure 21B:
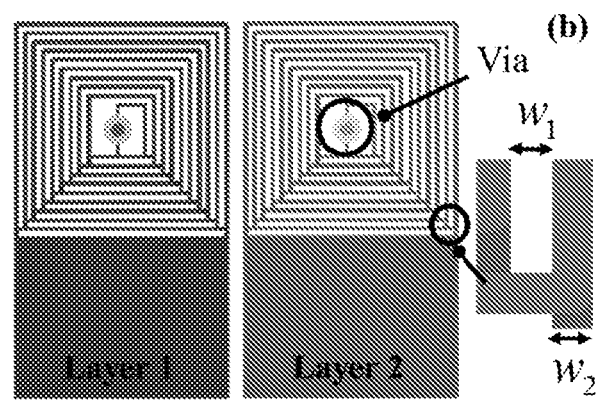
FIG. 21b shows the individual coil layers of an individual marker.

A monolithic, flexible printed circuit (FPC) structure is provided for each resonant circuit as seen in FIG. 21a. Inside each individual resonant circuit, a planar spiral inductor and a parallel plate capacitor are connected in series, as described above. The inductor is formed by arranging two layers of conductive copper paths into a planar spiral loop, and it works by converting the flux passing it into current. A parallel plate capacitor (FIG. 21a) is formed by sandwiching a dielectric layer between two conductive plates on both side of the FPC. The architecture is a monolithic structure where the inductor and capacitor are connected to each other during fabrication, and no extra manual fabrication is needed. The spiral layers are interconnected by a via, as seen in FIG. 21b. Standard FPC fabrication techniques were used to electroplate copper as the conductive layer, and polyimide was used as the dielectric layer with a dielectric constant of 3.4. The fabricated resonant circuit has a total dimension of 2.8 mm×5 mm in planar form.

Note that the marker's resonant frequency is sensitive to the mechanical dimension, where a change in dielectric thickness can result in a change in the resonant frequency. Therefore, the resonant frequency of the marker can be slightly different.

Analysis and Modeling for the Device

Figures 20A, 20B:
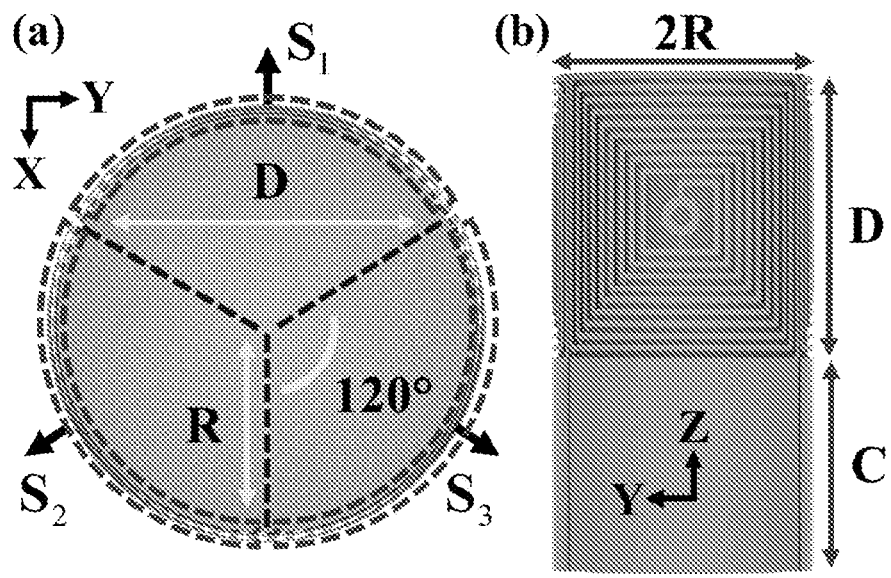

When a resonant circuit is wrapped on a cylinder as seen in FIG. 19 and FIGS. 20a and 20b, the changes in circuit's mechanical structure will lead to changes in its electrical characteristics. Thus, the resonant frequency for a curved shape is different from the planar shape. To design a circuit that has precise matching between the inductance and capacitance, it is necessary to understand the relationship between marker's electrical characteristics and geometrical layout.

Each planar spiral inductor is designed in square shape and has equivalent length and width. For a given surface area, an increase in the number of turns can increase the inductance more than the increase in resistance, hence increasing the quality factor which helps the MR signal amplification. Therefore, the number of turns is maximized according to the FPC fabrication limit (2.4 mil) until it reaches the central via (FIG. 21b). However, the formula cannot model the mutual coupling between the two layers accurately and is not valid in the bendable state.

Full-wave electromagnetic simulations were conducted with HFSS (HFSS, Ansoft Corp., Pittsburgh, USA) to estimate the RF characteristics of a defined structure under various electromagnetic circumstances. Taking advantage of finite element analysis, a quantitative estimate of the relationship between the bending curvature and inductance may be provided.

Multiple inductors with different geometrical layouts were fabricated to validate the FEA simulation results.

After the fabrication of the double layer inductors, S11 reflection coefficients were measured by using a Vector Network Analyzer (E5071A, Keysight Technologies, US) to electrically characterize it. The impedance of the inductor can be converted from the reflection coefficient r with single port measurement:

$$Z_m = Z_0 \cdot \left(\frac{1+\Gamma}{1-\Gamma}\right)$$

where $Z_o$ is the reference impedance of 50 ohms and $\Gamma$ is the reflection coefficient of the measured tracking marker. The calculated impedance is further converted into the inductance and quality factor of the multilayer inductor.

$$L_m = \frac{Im(Z_m)}{2\pi f}, Q_m = \frac{Im(Z_m)}{Re(Z_m)}$$

Curved Capacitor Analysis:
Input: dielectric constant, dielectric layer thickness, parallel plate area.
To complete the resonant circuit, the capacitor's appropriate capacitance is provided according to the equation below:

$$C = \frac{keA}{d}$$

Multiple capacitors with widths similar to the setup above were fabricated to validate the FEA simulation. It can be seen that with the increase in bending curvature the capacitance decreases.

Mutual Coupling:

When two markers are placed adjacently, magnetic flux coupling between them can introduce additional inductance to the marker, thus resulting in a resonant frequency shift. Although this coupling can be minimized by inserting a gap between the markers, it will reduce the inductor size hence another change to the resonant frequency.

The shift in resonant frequency is compensated by adjusting the capacitor size. FEA is used to estimate the mutual coupling effect and compute the required capacitor size.

The subject invention includes, but is not limited to, the following exemplified embodiments.

Embodiment 1. A magnetic resonance imaging inductively-coupled wireless tracking marker for three-dimensional positional tracking includes at least first and second conductive planar coils, the coils having a resonant frequency corresponding to a Larmor frequency of a magnetic resonance imaging scanner, each of the coils forming a spiral inductor, the at least first and second planar coils being coupled to each other to provide a mutual coupling effect between the at least first and second planar coils. Capacitors are connected to each of the planar coils and each of the planar coils being formed from a magnetic resonance imaging-compatible non-ferromagnetic material.

Embodiment 2. The device of embodiment 1, wherein the flexible printed circuit board comprises polyimide, polyether ether ketone (PEEK), or other conductive polyester film.

Embodiment 3. The device according to any of embodiments 1-2, wherein the plurality of flat planar spirals comprise copper, gold, silver, or other non-ferromagnetic material.

Embodiment 4. The device according to any of embodiments 1-3, wherein the device comprises four layers of flat planar spirals.

Embodiment 5. The device according to any of embodiments 1-4, wherein the device is connected to a photo-diode or photo-resister.

Embodiment 6. A method of fabricating an MR tracking device, the method comprising:
depositing a fundamental layer on the surface/cavity of an MRI-guided robotic system;
printing a conductive layer on the non-ferromagnetic material to form conductors for passive electronic components;
repeating the deposition of the non-ferromagnetic material and the printing to form a multilayered structure; and
encapsulating the multilayered structure in a biocompatible and magnetic resonance compatible material.

Embodiment 7. The method of embodiment 6, wherein the fundamental layer comprises polyimide, polyether ether ketone (PEEK), or other conductive polyester film.

Embodiment 8. The method according to any of embodiments 6-7, wherein the conductive layer comprises copper.

Embodiment 9. A method of fabricating an MR tracking device, the method comprising:
providing a plurality of double layered flexible printed circuit sheets;
printing non-ferromagnetic materials tracks on each side of each flexible printed circuit sheet;
connecting the tracks electrically through a plurality of vias comprising the non-ferromagnetic material;
encapsulating each flexible printed circuit sheet in a biocompatible and magnetic resonance compatible material; and
bonding the flexible printed circuit sheets together with an adhesive to form a multilayer coil.

Embodiment 10. The method of embodiment 9, wherein the flexible printed circuit sheets comprises polyimide, polyether ether ketone (PEEK), or other conductive polyester film.

Embodiment 11. The method according to any of embodiments 9-10, wherein the non-ferromagnetic material is copper.

Embodiment 12. The method according to any of embodiments 9-11, wherein the adhesive is an epoxy adhesive.

Embodiment 13. A method of determining the positions of multiple MR tracking markers with dynamic/changing geometrical layout, the method comprising: attaching multiple tracking markers to a 3D shape sensor; wherein a geometrical layout of the multiple tracking markers is obtained from a measurement from the 3D shape sensor; and wherein the obtained geometrical layout provides a unique solution during a back-projection computation process.

Embodiment 14. The method of embodiment 13, wherein the 3D shape sensor can be an FBG optic fiber or strain gauge.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

To validate the electrical properties of the MR tracking marker from the analytical approximation, electromagnetic field simulation (HFSS, Ansoft Corp., Pittsburgh, USA) with more precise estimation was used. The HFSS software was based on finite element analysis to predict the full-wave performance of a defined structure under electromagnetic circumstance, and was carried out at 63.87 MHz (1.5 T Larmor frequency). The simulation setup contained a MR tracking marker placed inside an air phantom (9 mm long, 5 mm width, and 8 mm high). An excitation of 1 W continuous wave signal at 63.87 MHz was applied at the terminal of the multilayer inductor. The sensitivity profiles were calculated with respect to the axial and sagittal slices in the center of the tracking marker.

The wireless fiducial marker positions were measured by using a tracking pulse-sequence that produces three 1D projections along the x, y, and z gradient axes. In the experiment, a head receiver coil was utilized with 8 receiving channels, and the magnetic flux from the fiducial markers was inductively coupled to all channels at the same time. In the experimental setup, the sum-of-squares (SOS) signal over the 8 channels was used. It can be observed that from a single projection along the x axis clearly shows two peaks, which is attributed by the 2 markers attached on the needle guide. A similar number of peaks can be observed along both the y and z axes.

The RF induced heating of the MR tracking marker was evaluated according to the ASTM protocol (ASTM F2182-09), the protocol covers the measurement of RF induced heating on or near a passive implant and its surroundings during MRI. The temperature of the MR tracking marker was recorded with a fluorescent temperature sensor connected to a measurement logging unit (PRB-MR1-10M-STM-MRI, OSENSA, Canada) via optical fiber at a sampling rate of 33 Hz. The measurement logging unit was positioned inside the MRI control room and the optical fibers were fed through the wave-guides to the scanner room. The tracking marker was then positioned on a phantom filled with agar gel.

Fast spin echo imaging (TE=7.16 ms, TR=400 ms, ETL=14, slice thickness=10 mm, Matrix=256×256, FOV=410×410 mm, flip angle=90°) was performed with the 1.5 T MRI scanner (Signa HDx, Software Release 16.0_V02, GE Healthcare, Waukesha, WI, USA) with the integrated head coil (receive). The sequence was conducted for approximately 15 minutes and produced an average whole body specific absorption rate (SAR) of 2 W/kg.

Example 1

Coil Parameters and Characterization

After the multilayer planar coil had been fabricated with a 495 nH inductance, it was soldered to a 12 pF non-ferromagnetic capacitor (Murata, Japan) to achieve resonant frequency at 1.5 T Larmor frequency. The S12 measured was taken as depicted in FIG. 12. It can be shown that a peak is located at 63.89 MHz, with quality factor of 27 computed by the resonant frequency divided by the 3 dB bandwidth.

Example 2

Micro Coil EM Finite-Element Analysis

The $B_1^-$ field of the MR fiducial marker on an insulating needle guide is shown in FIG. 13, with its profile extending approximately 5 mm perpendicular to the axial axis.

Example 3

MR Tracking Test

The MR tracking marker was tested in a 1.5 T GE Signa scanner. The wireless tracking marker was mounted on a standard 16×16 Lego plate with step size of 8 mm as shown in FIG. 15a. The setup was placed into a clinical 1.5 T MRI scanner (Signa HDx, Software Release 16.0_V02, GE Healthcare, Waukesha, WI, USA) with a standard 8-receiver imaging head coil, and was aligned with the scanner coordinate system by using the positioning laser. The MRI images were acquired with a gradient echo (GRE) sequence (TE=5.75 ms, TR=125 ms, slice thickness=3 mm, matrix 340×340, flip angle=1°, FOV=240×240 mm, pixel spacing=0.4688 mm) with gradient warp correction for gradient nonlinearities.

The accuracy and precision of the wireless marker were accessed from the MRI images with sub-pixel localization method, in which the Intensity Linear Interpolation (ILI) method was used to calculate the marker position. The method initially finds two-pixel values with half-maximum intensity, then interpolates to find the position along that dimension. Thirty images were taken at the isocenter and averaged as the reference image for later comparison. 6 images at a step size of 16 mm were taken along the x and y direction of the Lego plate respectively for post-processing in MATLAB. Note that shorter tracking update time of 35 ms is achievable by utilizing short 1D projection along the three-principle axis with comparable accuracy and precision. Such kind of tracking pulse sequence can be interleaved with an imaging pulse sequence to enable simultaneous imaging and tracking.

To analyze the tracking performance of the multilayer marker, MR images from the receiver channel with the highest peak-to-noise ratio was selected. The first 30 MR images taken with the MR tracking marker at the isocenter were analyzed with the sub-pixel localization method with Intensity Linear Interpolation. The inherent precision represented by the standard deviation is 0.12 mm (0.26 pixel). The results of the accuracy measurement are given in FIG. 15b. The plot shows the calculated 2D position difference between the expected and measured position against the marker's distance from the isocenter. The fitted solid line can be approximated as y=0.01·x in MATLAB with curve fitting tool. The increase in the position error can be explained by the inhomogeneity of the magnetic field created by the MRI scanner. Besides, it can be observed that the actual value scattered around the solid line, and was independent of the marker distance from isocenter. It can be observed that the accuracy of the wireless marker tracking is similar to active coil tracking, in which the tracking pulse sequence design and inhomogeneity of the imaging planars contribute most to the positional error.

In our current study, two applications have been developed as shown in FIG. 11. A 3D-printed plastic needle guided embedded with two wireless tracking markers can be visualized and tracked inside the MR image depicted in FIG. 11b. The tracking marker could also offer the tracking ability to a Ø3 mm catheter by attaching to the surface as depicted in FIG. 11d.

Example 4

Wireless Marker RF Safety

The RF induced heating of the MR tracking marker was evaluated according to the ASTM protocol (ASTM F2182-09), the protocol covers the measurement of RF-induced heating on or near a passive implant and its surroundings during MRI. The temperature of the MR tracking marker was recorded with a fluorescent temperature sensor connected to a measurement logging unit (PRB-MR1-10M-STM-MRI, OSENSA, Canada) via optical fiber at a sampling rate of 33 Hz. The measurement logging unit was positioned inside the MRI control room and the optical fibers were fed through the wave-guides to the scanner room. The tracking marker was then positioned on a phantom filled with agar gel. Fast spin echo imaging (IE=7.16 ms, TR=400 ms, ETL=14, slice thickness=10 mm, Matrix=256×256, FOV=410×410 mm, flip angle 90°) was performed with the 1.5 T MRI scanner (Signa HDx, Software Release 16.0_V02, GE Healthcare, Waukesha, WI, USA) with the integrated head coil (receive). The sequence was conducted for approximately 15 minutes and produced an average whole-body specific absorption rate (SAR) of 2 W/kg.

The maximum recorded temperature rise (measured at the location of the inductor) was 0.08° C. and did not exceed 0.6° C. temperature limit over the entire duration of the RF temperature test as shown in FIG. 16 which was performed according to the ASTM protocol.

Example 5

Orientation-Independent Device

After determining the required length of capacitor, the resonant circuit was fabricated monolithically by connecting them in parallel. Multiple test tracking markers were fabricated to assess their RF characteristics, hence its performance under MRI. A vector network analyzer was used with a wireless pick-up coil coupling to the marker to compute the transmission coefficient (S12). Both loaded and loaded characteristics were captured. The marker is designed to work at 1.5 T Larmor Frequency ($f_0$=63.87 MHz).

The tracking marker has uniform coupling with the MRI scanner RF coils in any orientation. To demonstrate the orientation independency, the marker's orientation was tested with a phantom experiment. The marker's orientations against 3-dimensional axis were change from 0° to 90° in steps of 5°. The signal intensity of the marker was calculated by the average signal intensity in the region of interest.

It should be understood that the examples and embodiments described herein are for illustrative purposes only and that various modifications or changes in light thereof will be suggested to persons skilled in the art and are to be included within the spirit and purview of this application.

REFERENCES

[1] W. M. Gedroyc, "Interventional magnetic resonance imaging," BJU Int, vol. 86 Suppl 1, pp. 174-80, July 2000.

[2] M. Bock et al., "MR-guided intravascular procedures: real-time parameter control and automated slice positioning with active tracking coils," (in eng), J Magn Reson Imaging, vol. 19, no. 5, pp. 580-9, May 2004.

[3] N. V. Tsekos, A. Khanicheh, E. Christoforou, and C. Mavroidis, "Magnetic resonance-compatible robotic and mechatronics systems for image-guided interventions and rehabilitation: a review study," (in eng), Annu Rev Biomed Eng, vol. 9, pp. 351-87, 2007.

[4] C. L. Dumoulin, S. P. Souza, and R. D. Darrow, "Real-Time Position Monitoring of Invasive Devices Using Magnetic-Resonance," (in English), Magnetic Resonance in Medicine, vol. 29, no. 3, pp. 411-415, March 1993.

[5] Y. Chen et al., "Design and Fabrication of MR-Tracked Metallic Stylet for Gynecologic Brachytherapy," IEEE/ASME Transactions on Mechatronics, vol. 21, no. 2, pp. 956-962, 2016.

[6] H. H. Quick et al., "Interventional magnetic resonance angiography with no strings attached: Wireless active catheter visualization," Magnetic Resonance in Medicine, vol. 53, no. 2, pp. 446-455, 2005.

[7] M. E. Ladd and H. H. Quick, "Reduction of resonant RF heating in intravascular catheters using coaxial chokes," (in eng), Magn Reson Med, vol. 43, no. 4, pp. 615-9, April 2000.

[8] S. Weiss, P. Vernickel, T. Schaeffter, V. Schulz, and B. Gleich, "Transmission line for improved RF safety of interventional devices," (in eng), Magn Reson Med, vol. 54, no. 1, pp. 182-9, July 2005.

[9] S. Weiss et al., "In vivo safe catheter visualization and slice tracking using an optically detunable resonant marker," Magn Reson Med, vol. 52, no. 4, pp. 860-8, October 2004.

[10] E. Y. Wong, Q. Zhang, J. L. Duerk, J. S. Lewin, and M. Wendt, "An optical system for wireless detuning of parallel resonant circuits," (in eng), J Magn Reson Imaging, vol. 12, no. 4, pp. 632-8, October 2000.

[11] R. A. Omary et al., "Real-Time MR Imaging-guided Passive Catheter Tracking with Use of Gadolinium-filled Catheters," Journal of Vascular and Interventional Radiology, vol. 11, no. 8, pp. 1079-1085.

[12] O. Unal, F. R. Korosec, R. Frayne, C. M. Strother, and C. A. Mistretta, "A rapid 2D time-resolved variable-rate k-space sampling MR technique for passive catheter tracking during endovascular procedures," Magnetic Resonance in Medicine, vol. 40, no. 3, pp. 356-362, 1998.

[13] F. K. Wacker, K. Reither, G. Branding, M. Wendt, and K. J. Wolf, "Magnetic resonance-guided vascular catheterization: feasibility using a passive tracking technique at 0.2 Telsa in a pig model," (in eng), J Magn Reson Imaging, vol. 10, no. 5, pp. 841-4, November 1999.

[14] W. R. Nitz, A. Oppelt, W. Renz, C. Manke, M. Lenhart, and J. Link, "On the heating of linear conductive structures as guide wires and catheters in interventional MRI," (in eng), J Magn Reson Imaging, vol. 13, no. 1, pp. 105-14, January 2001.

[15] W. R. Nitz, G. Brinker, D. Diehl, and G. Frese, "Specific Absorption Rate as a Poor Indicator of Magnetic Resonance-Related Implant Heating," Investigative Radiology, vol. 40, no. 12, pp. 773-776, 2005.

[16] A. Buecker, "Safety of MRI-guided vascular interventions," (in eng), Minim Invasive Ther Allied Technol, vol. 15, no. 2, pp. 65-70, 2006.

[17] M. B. Ooi, M. Aksoy, J. Maclaren, R. D. Watkins, and R. Bammer, "Prospective motion correction using inductively coupled wireless RF coils," Magn Reson Med, vol. 70, no. 3, pp. 639-47, September 2013.

[18] M. B. Ooi, J. Maclaren, M. AKSOY, R. Bammer, and R. D. Watkins, "Method for 3D motion tracking in an MRI scanner using inductively coupled microcoils," ed: Google Patents, 2014.

[19] W. G. Hurley and M. C. Duffy, "Calculation of self- and mutual impedances in planar sandwich inductors," (in English), Ieee Transactions on Magnetics, vol. 33, no. 3, pp. 2282-2290, May 1997.

[20] W. G. Hurley, M. C. Duffy, S. O'Reilly, and S. C. Mathuna, "Impedance formulas for planar magnetic structures with spiral windings," (in English), Ieee Transactions on Industrial Electronics, vol. 46, no. 2, pp. 271-278, April 1999.

[21] S. Babic and C. Akyel, "Improvement in calculation of the self- and mutual inductance of thin-wall solenoids and disk coils," (in English), Ieee Transactions on Magnetics, vol. 36, no. 4, pp. 1970-1975, July 2000.

[22] F. W. Grover, Inductance Calculations: Working Formulas and Tables. Dover Publications, 2004.

[23] S. Babic, F. Sirois, C. Akyel, and C. Girardi, "Mutual Inductance Calculation Between Circular Filaments Arbitrarily Positioned in Space: Alternative to Grover's Formula," (in English), Ieee Transactions on Magnetics, vol. 46, no. 9, pp. 3591-3600, September 2010.

[24] S. I. Babic and C. Akyel, "New analytic-numerical solutions for the mutual inductance of two coaxial circular coils with rectangular cross section in air," (in English), Ieee Transactions on Magnetics, vol. 42, no. 6, pp. 1661-1669, June 2006.

[25] W. G. Hurley, M. C. Duffy, J. Zhang, I. Lope, B. Kunz, and W. H. Wolfle, "A Unified Approach to the Calculation of Self- and Mutual-Inductance for Coaxial Coils in Air," (in English), Ieee Transactions on Power Electronics, vol. 30, no. 11, pp. 6155-6162, November 2015.

[26] H. Greenhouse, "Design of Planar Rectangular Microelectronic Inductors," IEEE Transactions on Parts, Hybrids, and Packaging, vol. 10, no. 2, pp. 101-109, 1974.

[27] J. Uei-Ming and M. Ghovanloo, "Modeling and optimization of printed spiral coils in air, saline, and muscle tissue environments," IEEE Trans Biomed Circuits Syst, vol. 3, no. 5, pp. 339-47, October 2009.

[28] ASTM F2182-09, Standard Test Method for Measurement of Radio Frequency Induced Heating Near Passive Implants During Magnetic Resonance Imaging, ASTM International, West Conshohocken, PA, 2009.

[29] M. Rea, D. McRobbie, H. Elhawary, Z. T. Tse, M. Lamperth, and I. Young, "Sub-pixel localisation of passive micro-coil fiducial markers in interventional MRI," (in eng), Magma, vol. 22, no. 2, pp. 71-6, April 2009.

What is claimed is:

1. A magnetic resonance imaging inductively-coupled wireless tracking marker for three-dimensional positional tracking comprising:
    a plurality of double layered flexible printed circuit sheets (202), wherein each of the double layered flexible printed circuit sheets (202) is encapsulated in a biocompatible and magnetic resonance compatible material;
    a first conductive planar coil (203) and a second conductive planar coil (203) disposed on a first side and a second side, respectively, of each of the double layered flexible printed circuit sheets (202), wherein each of the double layered flexible printed circuit sheets (202) is bonded together to at least one other of the double layered flexible printed circuit sheets (202) with an adhesive to form a multilayer coil, wherein each of the first conductive planar coil and the second conductive planar coil has a resonant frequency corresponding to a Larmor frequency of a magnetic resonance imaging scanner, wherein each of the first conductive planar coil forms a first spiral inductor, wherein each of the second conductive planar coil forms a second spiral inductor, wherein the first conductive planar coil (203) and the second planar coil (203) are respectively coupled to each other to provide a mutual coupling effect therebetween;
    a first planar parallel plate capacitor (205) connected to each of the first conductive planar coils (203) and a second planar parallel plate capacitor (205) connected to each of the second conductive planar coils (203); and
    a plurality of vias comprising a magnetic resonance imaging-compatible non-ferromagnetic material and electrically connecting the first conductive planar coil (203) of each double layered flexible printed circuit sheet (202) to the second conductive planar coil (203) of said double layered flexible printed circuit sheet (202) and to the first conductive planar coil (203) and the second conductive planar coil (203) of each other double layered flexible printed circuit sheet (202),
    wherein each of the first conductive planar coil (203) and the second conductive planar coil (203) comprising the magnetic resonance imaging-compatible non-ferromagnetic material.

2. The magnetic resonance imaging inductively-coupled wireless tracking marker according to claim 1, wherein each of the double layered flexible printed circuit sheets (202) comprises a printed circuit board.

3. The magnetic resonance imaging inductively-coupled wireless tracking marker according to claim 2, wherein each printed circuit board of each of the double layered flexible printed circuit sheets (202) comprises polyimide, polyether ether ketone (PEEK), or other conductive polyester film.

4. The magnetic resonance imaging inductively-coupled wireless tracking marker of claim 1, wherein the non-ferromagnetic material is selected from copper, gold, and silver.

5. The magnetic resonance imaging inductively-coupled wireless tracking marker of claim 1, wherein the plurality of double layered flexible printed circuit sheets (202) comprises exactly two double layered flexible printed circuit sheets (202).

6. The magnetic resonance imaging inductively-coupled wireless tracking marker of claim 1, wherein the first planar parallel plate capacitor (205) and the first spiral inductor are both connected to a first optical switch that is a photo-diode or photo-resistor, and
    wherein the second planar parallel plate capacitor (205) and the second spiral inductor are both connected to a second optical switch that is a photodiode or a photo-resistor.

7. The magnetic resonance imaging inductively-coupled wireless tracking marker according to claim 6, wherein the first optical switch is a photoresistor, and
    wherein the second optical switch is a photoresistor.

8. The magnetic resonance imaging inductively-coupled wireless tracking marker according to claim 6, wherein the first optical switch is a photodiode, and wherein the second optical switch is a photodiode.

9. A substantially orientation-independent magnetic resonance imaging inductively-coupled wireless device for three-dimensional positional tracking comprising three or more of the markers of claim 1 positioned in a curved 360-degree array around a substantially cylindrical core.

10. The substantially orientation-independent magnetic resonance imaging inductively-coupled wireless device of claim 9, wherein each of the markers has a surface normal vector such that each surface normal vector shares a same centroid and are separated by 120° alternatively in a same plane.

11. The substantially orientation-independent magnetic resonance imaging inductively-coupled wireless device of claim 7, comprising an odd number of markers greater than three.

12. The magnetic resonance imaging inductively-coupled wireless tracking marker according to claim 1, wherein the first conductive planar coil (203) is formed as a first printed track on the first side of each of the double layered flexible printed circuit sheets (202), and wherein the second conductive planar coil (203) is formed as a second printed track on the second side of each of the double layered flexible printed circuit sheets (202).

13. A method of fabricating the marker of claim 1, the method comprising:

providing a plurality of double layered flexible printed circuit sheets;

printing non-ferromagnetic material tracks on each side of each flexible printed circuit sheet;

connecting the tracks electrically through a plurality of vias comprising the non-ferromagnetic material;

encapsulating each flexible printed circuit sheet in a biocompatible and magnetic resonance compatible material; and bonding the flexible printed circuit sheets together with an adhesive to form a multilayer coil.

14. The method of claim 13, wherein the flexible printed circuit sheets comprise polyimide, polyether ether ketone (PEEK), or a conductive polyester film.

15. The method of claim 13, wherein the non-ferromagnetic material is copper.

16. The method of claim 13, wherein the adhesive is an epoxy adhesive.

17. A method of determining the positions of multiple magnetic resonance (MR) tracking markers with a dynamic/changing geometrical layout, the method comprising:

attaching a plurality of markers of claim 1 to a three dimensional (3D) shape sensor;

wherein a geometrical layout of the plurality of markers is obtained from a measurement from the 3D shape sensor; and wherein the obtained geometrical layout provides a unique solution during a back-projection computation process.

18. The method of claim 17, wherein the 3D shape sensor is a fiber Bragg grating optic fiber or strain gauge.

* * * * *